United States Patent
Quisenberry et al.

(10) Patent No.: US 10,300,180 B1
(45) Date of Patent: May 28, 2019

(54) WOUND CARE AND INFUSION METHOD AND SYSTEM UTILIZING A THERAPEUTIC AGENT

(71) Applicant: ThermoTek, Inc., Flower Mound, TX (US)

(72) Inventors: Tony Quisenberry, Highland Village, TX (US); Sam K. McSpadden, Austin, TX (US); Niran Balachandran, Lewisville, TX (US); Robert K. Lasalle, Gainesville, TX (US); Thomas C. Anderson, Frisco, TX (US); Kathryn Davis, Trophy Club, TX (US)

(73) Assignee: ThermoTek, Inc., Flower Mound, TX (US)

( * ) Notice: Subject to any disclaimer, the term of this patent is extended or adjusted under 35 U.S.C. 154(b) by 13 days.

(21) Appl. No.: 15/730,421

(22) Filed: Oct. 11, 2017

Related U.S. Application Data

(63) Continuation-in-part of application No. 14/197,324, filed on Mar. 5, 2014, now Pat. No. 10,016,583.

(Continued)

(51) Int. Cl.
*A61M 1/00* (2006.01)
*A61M 35/00* (2006.01)
(Continued)

(52) U.S. Cl.
CPC ........ *A61M 1/0084* (2013.01); *A61M 1/0092* (2014.02); *A61M 35/00* (2013.01);
(Continued)

(58) Field of Classification Search
CPC .............. A61M 1/0058; A61M 1/0084; A61M 2202/0208; A61M 2205/3368; A61M 2205/36
See application file for complete search history.

(56) References Cited

U.S. PATENT DOCUMENTS 773,828 A 11/1904 Titus
2,110,022 A 3/1938 Kliesrath
(Continued)

FOREIGN PATENT DOCUMENTS

CH 670 541 6/1989
DE 35 22 127 1/1987
(Continued)

OTHER PUBLICATIONS

U.S. Appl. No. 12/730,060, Parish et al.
(Continued)

*Primary Examiner* — Kai Weng
(74) *Attorney, Agent, or Firm* — Winstead PC

(57) ABSTRACT

A wound-care system includes a first pump fluidly coupled to an oxygen source. An oxygen concentrator is fluidly coupled to the first pump. A humidification system is fluidly coupled to the oxygen concentrator. A wound dressing is fluidly coupled to the humidification system and to an exudate chamber. A negative-pressure tube fluidly is coupled to the exudate chamber. A first valve is disposed between the first pump and the oxygen concentrator. A second valve is disposed between the oxygen concentrator and the wound dressing. A third valve is disposed in the negative-pressure tube. Selective activation of the first pump, the first valve, the second valve, and the third valve facilitates delivery of at least one of individual, sequential, or simultaneous negative-pressure treatment and oxygen-rich fluid treatment to the wound via the wound dressing.

13 Claims, 23 Drawing Sheets

Related U.S. Application Data

(60) Provisional application No. 61/776,328, filed on Mar. 11, 2013.

(51) Int. Cl.
*A61N 5/06* (2006.01)
*A61M 39/24* (2006.01)

(52) U.S. Cl.
CPC ............ *A61N 5/0624* (2013.01); *A61M 39/24* (2013.01); *A61M 2202/0208* (2013.01); *A61M 2205/3337* (2013.01); *A61M 2205/3344* (2013.01); *A61M 2205/3592* (2013.01); *A61M 2205/3673* (2013.01); *A61M 2205/75* (2013.01); *A61N 2005/0651* (2013.01); *A61N 2005/0661* (2013.01)

(56) References Cited

U.S. PATENT DOCUMENTS

| | | |
|---|---|---|
| 2,504,308 A | 4/1950 | Donkle, Jr. |
| 3,014,117 A | 12/1961 | Madding |
| 3,164,152 A | 1/1965 | Vere |
| 3,179,106 A | 4/1965 | Meredith |
| 3,345,641 A | 10/1967 | Jennings |
| 3,367,319 A | 2/1968 | Carter, Jr. |
| 3,548,809 A | 12/1970 | Conti |
| 3,608,091 A | 9/1971 | Olson et al. |
| 3,660,849 A | 5/1972 | Jonnes et al. |
| 3,736,764 A | 6/1973 | Chambers et al. |
| 3,738,702 A | 6/1973 | Jacobs |
| 3,744,053 A | 7/1973 | Parker et al. |
| 3,744,555 A | 7/1973 | Fletcher et al. |
| 3,862,629 A | 1/1975 | Rotta |
| 3,894,213 A | 7/1975 | Agarwala |
| 4,006,604 A | 2/1977 | Seff |
| 4,013,069 A | 3/1977 | Hasty |
| 4,029,087 A | 6/1977 | Dye et al. |
| 4,206,751 A | 6/1980 | Schneider |
| 4,224,941 A | 9/1980 | Stivala |
| 4,375,217 A | 3/1983 | Arkans |
| 4,402,312 A | 9/1983 | Villari et al. |
| 4,419,988 A | 12/1983 | Mummert |
| 4,459,468 A | 7/1984 | Bailey |
| 4,459,822 A | 7/1984 | Pasternack |
| 4,471,787 A | 9/1984 | Bentall |
| 4,503,484 A | 3/1985 | Moxon |
| 4,523,594 A | 6/1985 | Kuznetz |
| 4,547,906 A | 10/1985 | Nishida et al. |
| 4,590,925 A | 5/1986 | Dillon |
| 4,597,384 A | 7/1986 | Whitney |
| 4,608,041 A | 8/1986 | Nielsen |
| D285,821 S | 9/1986 | Kneisley |
| D288,372 S | 2/1987 | Adams |
| 4,660,388 A | 4/1987 | Greene, Jr. |
| 4,738,249 A | 4/1988 | Linman et al. |
| D295,897 S | 5/1988 | Thimm-Kelly |
| 4,741,338 A | 5/1988 | Miyamae |
| 4,795,435 A | 1/1989 | Steer |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Horne et al. |
| 4,926,881 A | 5/1990 | Ichinomiya et al. |
| 4,962,761 A | 10/1990 | Golden |
| 4,979,375 A | 10/1990 | Nathans et al. |
| 4,969,881 A | 11/1990 | Viesturs |
| 4,989,589 A | 2/1991 | Pekanmaki et al. |
| 4,995,698 A | 2/1991 | Myers |
| 4,996,970 A | 3/1991 | Legare |
| 5,044,364 A | 9/1991 | Crowther |
| 5,051,562 A | 9/1991 | Bailey et al. |
| D320,872 S | 10/1991 | McCrane |
| 5,062,414 A | 11/1991 | Grim |
| 5,067,040 A | 11/1991 | Fallik |
| 5,080,089 A | 1/1992 | Mason et al. |
| 5,090,409 A | 2/1992 | Genis |
| 5,092,271 A | 3/1992 | Kleinsasser |
| 5,097,829 A | 3/1992 | Quisenberry |
| 5,106,373 A | 4/1992 | Augustine et al. |
| 5,112,045 A | 5/1992 | Mason et al. |
| 5,117,812 A | 6/1992 | McWhorter |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,315,994 A | 5/1994 | Guibert et al. |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| D354,138 S | 1/1995 | Kelly |
| D357,747 S | 4/1995 | Kelly |
| 5,402,542 A | 4/1995 | Viard |
| 5,405,370 A | 4/1995 | Irani |
| 5,405,371 A | 4/1995 | Augustine et al. |
| 5,407,421 A | 4/1995 | Goldsmith |
| D358,216 S | 5/1995 | Dye |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,466,250 A | 11/1995 | Johnson, Jr. et al. |
| 5,496,262 A | 3/1996 | Johnson, Jr. et al. |
| 5,496,357 A | 3/1996 | Jensen et al. |
| 5,505,726 A | 4/1996 | Meserol |
| 5,507,792 A | 4/1996 | Mason |
| 5,509,894 A | 4/1996 | Mason et al. |
| 5,514,079 A | 5/1996 | Dillon |
| 5,528,485 A | 6/1996 | Devilbiss et al. |
| 5,561,981 A | 10/1996 | Quisenberry et al. |
| 5,566,062 A | 10/1996 | Quisenberry et al. |
| D376,013 S | 11/1996 | Sandman et al. |
| 5,578,022 A | 11/1996 | Scherson et al. |
| 5,588,954 A | 12/1996 | Ribando et al. |
| 5,591,200 A | 1/1997 | Cone et al. |
| 5,636,643 A | 6/1997 | Argenta et al. |
| D380,874 S | 7/1997 | Caswell |
| 5,645,081 A | 7/1997 | Argenta et al. |
| 5,648,716 A | 7/1997 | Devilbiss et al. |
| D383,546 S | 9/1997 | Amis et al. |
| D383,547 S | 9/1997 | Mason et al. |
| D383,848 S | 9/1997 | Mason et al. |
| 5,662,695 A | 9/1997 | Mason et al. |

(56) References Cited

U.S. PATENT DOCUMENTS

| | | | |
|---|---|---|---|
| 5,669,872 A | 9/1997 | Fox | |
| 5,672,152 A | 9/1997 | Mason et al. | |
| 5,675,473 A | 10/1997 | McDunn et al. | |
| 5,682,748 A | 11/1997 | DeVilbiss et al. | |
| 5,689,957 A | 11/1997 | DeVilbiss et al. | |
| 5,690,849 A | 11/1997 | DeVilbiss et al. | |
| 5,711,029 A | 1/1998 | Visco et al. | |
| 5,711,155 A | 1/1998 | DeVilbiss et al. | |
| D393,073 S | 3/1998 | Downing et al. | |
| 5,731,954 A | 3/1998 | Cheon | |
| 5,733,321 A | 3/1998 | Brink | |
| D394,707 S | 5/1998 | Tsubooka | |
| 5,755,755 A | 5/1998 | Panyard | |
| 5,772,618 A | 6/1998 | Mason et al. | |
| 5,782,780 A | 7/1998 | Mason et al. | |
| 5,795,312 A | 8/1998 | Dye | |
| 5,807,294 A | 9/1998 | Cawley et al. | |
| 5,827,208 A | 10/1998 | Mason | |
| 5,831,824 A | 11/1998 | McDunn et al. | |
| D403,779 S | 1/1999 | Davis et al. | |
| D404,490 S | 1/1999 | Tripolsky | |
| D405,884 S | 2/1999 | Roper | |
| 5,865,841 A | 2/1999 | Kolen et al. | |
| 5,871,526 A | 2/1999 | Gibbs et al. | |
| 5,890,371 A | 4/1999 | Rajasubramanian et al. | |
| 5,897,581 A | 4/1999 | Fronda et al. | |
| 5,901,037 A | 5/1999 | Hamilton et al. | |
| 5,923,533 A | 7/1999 | Olson | |
| 5,947,914 A | 9/1999 | Augustine | |
| 5,980,561 A | 11/1999 | Kolen et al. | |
| 5,989,285 A | 11/1999 | DeVilbiss et al. | |
| 6,007,559 A | 12/1999 | Arkans | |
| 6,055,157 A | 4/2000 | Bartilson | |
| 6,058,010 A | 5/2000 | Schmidt et al. | |
| 6,058,712 A | 5/2000 | Rajasubramanian et al. | |
| 6,080,120 A | 6/2000 | Sandman et al. | |
| D428,153 S | 7/2000 | Davis | |
| D430,288 S | 8/2000 | Mason et al. | |
| D430,289 S | 8/2000 | Mason et al. | |
| 6,117,164 A | 9/2000 | Gildersleeve et al. | |
| 6,125,036 A | 9/2000 | Kang et al. | |
| 6,129,688 A | 10/2000 | Arkans | |
| 6,135,116 A | 10/2000 | Vogel et al. | |
| 6,156,059 A | 12/2000 | Olofsson | |
| 6,176,869 B1 | 1/2001 | Mason et al. | |
| 6,178,562 B1 | 1/2001 | Elkins | |
| 6,186,977 B1 | 2/2001 | Andrews et al. | |
| 6,231,532 B1 | 5/2001 | Watson et al. | |
| 6,235,049 B1 | 5/2001 | Nazerian | |
| 6,238,427 B1 | 5/2001 | Matta | |
| 6,260,890 B1 | 7/2001 | Mason | |
| 6,270,481 B1 | 8/2001 | Mason et al. | |
| 6,295,819 B1 | 10/2001 | Mathiprakasam et al. | |
| 6,305,180 B1 | 10/2001 | Miller et al. | |
| 6,312,453 B1 | 11/2001 | Stefanile et al. | |
| 6,319,114 B1 | 11/2001 | Nair et al. | |
| 6,352,550 B1 | 3/2002 | Gildersleeve et al. | |
| 6,358,219 B1 | 3/2002 | Arkans | |
| 6,368,592 B1 | 4/2002 | Colton et al. | |
| 6,436,064 B1 | 8/2002 | Kloecker | |
| 6,443,978 B1 | 9/2002 | Zharov | |
| 6,462,949 B1 | 10/2002 | Parish, IV et al. | |
| 6,468,237 B1 | 10/2002 | Lina | |
| 6,508,831 B1 | 1/2003 | Kushnir | |
| D472,322 S | 3/2003 | Hoglund et al. | |
| D473,315 S | 4/2003 | Miros et al. | |
| D473,656 S | 4/2003 | Miros et al. | |
| D473,948 S | 4/2003 | Elkins et al. | |
| 6,551,264 B1 | 4/2003 | Cawley et al. | |
| 6,551,347 B1 | 4/2003 | Elkins | |
| D474,544 S | 5/2003 | Hoglund et al. | |
| 6,562,060 B1 | 5/2003 | Momtaheni | |
| 6,596,016 B1 | 7/2003 | Vreman et al. | |
| 6,648,904 B2 | 11/2003 | Altshuler et al. | |
| D484,601 S | 12/2003 | Griffiths et al. | |
| D484,602 S | 12/2003 | Griffiths et al. | |
| 6,660,027 B2 | 12/2003 | Gruszecki et al. | |
| 6,667,883 B1 | 12/2003 | Solis et al. | |
| 6,675,072 B1 | 1/2004 | Kerem | |
| D486,870 S | 2/2004 | Mason | |
| 6,695,823 B1 | 2/2004 | Lina et al. | |
| 6,719,713 B2 | 4/2004 | Mason | |
| 6,719,728 B2 | 4/2004 | Mason et al. | |
| 6,736,787 B1 | 5/2004 | McEwen et al. | |
| 6,740,146 B2 * | 5/2004 | Simonds | B01D 53/0415 95/130 |
| D492,411 S | 6/2004 | Bierman | |
| 6,775,137 B2 | 8/2004 | Chu et al. | |
| D496,108 S | 9/2004 | Machin et al. | |
| 6,789,024 B1 | 9/2004 | Kochan, Jr. et al. | |
| 6,802,823 B2 | 10/2004 | Mason | |
| D499,846 S | 12/2004 | Cesko | |
| 6,834,712 B2 | 12/2004 | Parish et al. | |
| 6,846,295 B1 | 1/2005 | Ben-Nun | |
| 6,848,498 B2 | 2/2005 | Seki et al. | |
| 6,855,158 B2 | 2/2005 | Stolpmann | |
| 6,893,414 B2 | 5/2005 | Goble et al. | |
| D506,553 S | 6/2005 | Tesluk | |
| 6,935,409 B1 | 8/2005 | Parish, IV et al. | |
| 6,936,019 B2 | 8/2005 | Mason | |
| D510,140 S | 9/2005 | Brown | |
| 6,945,988 B1 | 9/2005 | Jones | |
| D510,626 S | 10/2005 | Krahner et al. | |
| D515,218 S | 2/2006 | McGuire et al. | |
| 7,004,915 B2 | 2/2006 | Boynton et al. | |
| D523,147 S | 6/2006 | Tesluk | |
| 7,066,949 B2 | 6/2006 | Gammons et al. | |
| 7,081,128 B2 | 7/2006 | Hart et al. | |
| D533,668 S | 12/2006 | Brown | |
| 7,195,624 B2 | 3/2007 | Lockwood et al. | |
| 7,198,046 B1 | 4/2007 | Argenta et al. | |
| 7,216,651 B2 | 5/2007 | Argenta et al. | |
| D551,351 S | 9/2007 | Silva | |
| D551,352 S | 9/2007 | Frangi | |
| 7,306,568 B2 | 12/2007 | Diana | |
| 7,354,411 B2 | 4/2008 | Perry et al. | |
| D568,482 S | 5/2008 | Gramza et al. | |
| D569,985 S | 5/2008 | Ganapathy et al. | |
| 7,427,153 B1 | 9/2008 | Jacobs et al. | |
| 7,429,252 B2 | 9/2008 | Sarangapani | |
| 7,484,552 B2 | 2/2009 | Pfahnl | |
| 7,492,252 B2 | 2/2009 | Maruyama | |
| 7,524,286 B2 | 4/2009 | Johnson | |
| 7,532,953 B2 | 5/2009 | Vogel | |
| 7,553,306 B1 | 6/2009 | Hunt et al. | |
| D595,620 S | 7/2009 | Kingsbury | |
| D601,707 S | 10/2009 | Chouiller | |
| 7,608,066 B2 | 10/2009 | Vogel | |
| 7,618,382 B2 | 11/2009 | Vogel et al. | |
| D608,006 S | 1/2010 | Avitable et al. | |
| D612,947 S | 3/2010 | Turtzo et al. | |
| D613,870 S | 4/2010 | Shust | |
| 7,717,869 B2 | 5/2010 | Eischen, Sr. | |
| D618,358 S | 6/2010 | Avitable et al. | |
| D619,267 S | 7/2010 | Beckwith et al. | |
| D620,122 S | 7/2010 | Cotton | |
| 7,763,000 B2 | 7/2010 | Risk, Jr. et al. | |
| 7,799,004 B2 | 9/2010 | Tumey | |
| 7,804,686 B2 | 9/2010 | Parish et al. | |
| D625,018 S | 10/2010 | Smith et al. | |
| D626,241 S | 10/2010 | Sagnip et al. | |
| D626,242 S | 10/2010 | Sagnip et al. | |
| D626,243 S | 10/2010 | Sagnip et al. | |
| D626,245 S | 10/2010 | Sagnip et al. | |
| 7,811,269 B2 | 10/2010 | Boynton et al. | |
| D627,896 S | 11/2010 | Matsuo et al. | |
| D628,300 S | 11/2010 | Caden | |
| 7,837,673 B2 | 11/2010 | Vogel | |
| D630,759 S | 1/2011 | Matsuo et al. | |
| 7,867,206 B2 | 1/2011 | Lockwood et al. | |
| 7,871,387 B2 | 1/2011 | Tordella et al. | |
| D631,971 S | 2/2011 | Turtzo et al. | |
| D633,657 S | 3/2011 | Oban | |
| D634,437 S | 3/2011 | Gramza et al. | |

(56) References Cited

U.S. PATENT DOCUMENTS

| | | |
|---|---|---|
| D634,851 S | 3/2011 | Chiang |
| D635,266 S | 3/2011 | Chiang |
| D635,267 S | 3/2011 | Chiang |
| 7,896,864 B2 | 3/2011 | Lockwood et al. |
| 7,896,910 B2 | 3/2011 | Schirrmacher et al. |
| 7,909,861 B2 | 3/2011 | Balachandran et al. |
| D636,497 S | 4/2011 | Giaccone |
| D638,950 S | 5/2011 | Janzon |
| D640,380 S | 6/2011 | Tweardy et al. |
| D640,381 S | 6/2011 | Tweardy et al. |
| 7,959,588 B1 | 6/2011 | Wolpa |
| 8,007,491 B2 | 8/2011 | Pinto et al. |
| D649,648 S | 11/2011 | Cavalieri et al. |
| 8,052,630 B2 | 11/2011 | Kloecker et al. |
| 8,084,663 B2 | 12/2011 | Watson, Jr. |
| 8,088,113 B2 | 1/2012 | Scherson et al. |
| 8,100,956 B2 | 1/2012 | Quisenberry et al. |
| 8,109,981 B2 | 2/2012 | Gertner et al. |
| D655,420 S | 3/2012 | Bowles |
| D655,821 S | 3/2012 | Matsuo |
| 8,128,672 B2 | 3/2012 | Quisenberry et al. |
| 8,142,486 B2 | 3/2012 | Quisenberry et al. |
| D657,063 S | 4/2012 | Chiang |
| 8,157,792 B2 | 4/2012 | Dolliver et al. |
| D660,438 S | 5/2012 | Kennedy et al. |
| D660,439 S | 5/2012 | Chen et al. |
| D662,212 S | 6/2012 | Quisenberry |
| D662,213 S | 6/2012 | Quisenberry |
| D662,214 S | 6/2012 | Quisenberry |
| 8,202,262 B2 | 6/2012 | Lina et al. |
| D663,850 S | 7/2012 | Joseph |
| D664,260 S | 7/2012 | Quisenberry |
| D665,088 S | 8/2012 | Joseph |
| D665,470 S | 8/2012 | Galbraith |
| D666,258 S | 8/2012 | Campbell |
| D666,301 S | 8/2012 | Joseph |
| 8,240,885 B2 | 8/2012 | Miller |
| 8,248,798 B2 | 8/2012 | Parish et al. |
| D679,023 S | 3/2013 | Quisenberry |
| 8,425,580 B2 | 4/2013 | Quisenberry et al. |
| D683,042 S | 5/2013 | Quisenberry |
| 8,444,581 B1 | 5/2013 | Maxon-Maldonado et al. |
| 8,449,483 B2 | 5/2013 | Eddy |
| 8,485,995 B1 | 7/2013 | Maxon-Maldonado |
| 8,529,613 B2 | 9/2013 | Radziunas et al. |
| 8,569,566 B2 | 10/2013 | Blott et al. |
| 8,574,278 B2 | 11/2013 | Quisenberry |
| 8,632,576 B2 | 1/2014 | Quisenberry |
| 8,753,300 B2 | 6/2014 | Deshpande |
| 8,753,383 B2 | 6/2014 | Parish et al. |
| 8,758,419 B1 | 6/2014 | Quisenberry et al. |
| 8,772,567 B2 | 7/2014 | Eckstein et al. |
| 8,778,005 B2 | 7/2014 | Parish et al. |
| 8,827,935 B2 | 9/2014 | Maxon-Maldonado |
| 8,834,393 B2 | 9/2014 | Maxon-Maldonado et al. |
| 8,940,034 B2 | 1/2015 | Quisenberry |
| 9,101,463 B2 | 8/2015 | Stormby |
| 9,114,055 B2 | 8/2015 | Edelman et al. |
| 9,119,705 B2 | 9/2015 | Parish et al. |
| 9,132,057 B2 | 9/2015 | Wilford et al. |
| 9,180,041 B2 | 11/2015 | Parish et al. |
| 9,192,539 B2 | 11/2015 | Parish et al. |
| 9,669,233 B2 | 6/2017 | Quisenberry et al. |
| 2001/0018604 A1 | 8/2001 | Elkins |
| 2001/0039439 A1 | 11/2001 | Elkins et al. |
| 2002/0116041 A1 | 8/2002 | Daoud |
| 2002/0143373 A1 | 10/2002 | Courtnage et al. |
| 2003/0050594 A1 | 3/2003 | Zamierowski |
| 2003/0083610 A1 | 5/2003 | McGrath et al. |
| 2003/0089486 A1 | 5/2003 | Parish et al. |
| 2003/0089487 A1 | 5/2003 | Parish, IV et al. |
| 2003/0125649 A1 | 7/2003 | McIntosh et al. |
| 2003/0127215 A1 | 7/2003 | Parish, IV et al. |
| 2003/0135252 A1 | 7/2003 | MacHold et al. |
| 2003/0139255 A1 | 7/2003 | Lina |
| 2003/0163183 A1 | 8/2003 | Carson |
| 2003/0171703 A1 | 9/2003 | Grim et al. |
| 2003/0176822 A1 | 9/2003 | Morgenlander |
| 2003/0191437 A1 | 10/2003 | Knighton et al. |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0068310 A1 | 4/2004 | Edelman |
| 2004/0099407 A1 | 5/2004 | Parish, IV et al. |
| 2004/0133135 A1 | 7/2004 | Diana |
| 2004/0176805 A1 | 9/2004 | Whelan et al. |
| 2004/0186535 A1 | 9/2004 | Knowlton |
| 2004/0193218 A1 | 9/2004 | Butler |
| 2004/0210176 A1 | 10/2004 | Diana |
| 2004/0221604 A1 | 11/2004 | Ota et al. |
| 2004/0260231 A1 | 12/2004 | Goble et al. |
| 2005/0004636 A1 | 1/2005 | Noda et al. |
| 2005/0006061 A1 | 1/2005 | Quisenberry et al. |
| 2005/0033390 A1 | 2/2005 | McConnell |
| 2005/0039887 A1 | 2/2005 | Parish, IV et al. |
| 2005/0070828 A1 | 3/2005 | Hampson et al. |
| 2005/0070835 A1 | 3/2005 | Joshi |
| 2005/0080465 A1 | 4/2005 | Zelickson et al. |
| 2005/0126578 A1 | 6/2005 | Garrison et al. |
| 2005/0133214 A1 | 6/2005 | Pfahnl |
| 2005/0143797 A1 | 6/2005 | Parish et al. |
| 2005/0177093 A1 | 8/2005 | Barry et al. |
| 2005/0182364 A1 | 8/2005 | Burchman |
| 2005/0187500 A1 | 8/2005 | Perry et al. |
| 2005/0256556 A1 | 11/2005 | Schirrmacher et al. |
| 2005/0274120 A1 | 12/2005 | Quisenberry et al. |
| 2005/0284615 A1 | 12/2005 | Parish et al. |
| 2006/0034053 A1 | 2/2006 | Parish et al. |
| 2006/0058714 A1 | 3/2006 | Rhoades |
| 2006/0116620 A1 | 6/2006 | Oyaski |
| 2006/0167531 A1 | 7/2006 | Gertner et al. |
| 2006/0241549 A1 | 10/2006 | Sunnen |
| 2006/0253089 A1 | 11/2006 | Lin |
| 2006/0276845 A1 | 12/2006 | George et al. |
| 2006/0282028 A1 | 12/2006 | Howard et al. |
| 2007/0032778 A1 | 2/2007 | Heaton et al. |
| 2007/0068651 A1 | 3/2007 | Gammons et al. |
| 2007/0112401 A1 | 5/2007 | Balachandran et al. |
| 2007/0118194 A1 | 5/2007 | Mason et al. |
| 2007/0129658 A1 | 6/2007 | Hampson et al. |
| 2007/0233209 A1 | 10/2007 | Whitehurst |
| 2007/0260162 A1 | 11/2007 | Meyer et al. |
| 2007/0282249 A1 | 12/2007 | Quisenberry |
| 2008/0058911 A1 | 3/2008 | Parish et al. |
| 2008/0064992 A1 | 3/2008 | Stewart et al. |
| 2008/0071330 A1 | 3/2008 | Quisenberry |
| 2008/0082029 A1 | 4/2008 | Diana |
| 2008/0103397 A1 | 5/2008 | Barak |
| 2008/0103422 A1 | 5/2008 | Perry et al. |
| 2008/0125775 A1 | 5/2008 | Morris |
| 2008/0132816 A1 | 6/2008 | Kane et al. |
| 2008/0132976 A1 | 6/2008 | Kane et al. |
| 2008/0249559 A1 | 10/2008 | Brown et al. |
| 2008/0262399 A1 | 10/2008 | Kovelman et al. |
| 2008/0319362 A1 | 12/2008 | Joseph |
| 2009/0069731 A1 | 3/2009 | Parish et al. |
| 2009/0109622 A1 | 4/2009 | Parish et al. |
| 2009/0149821 A1 | 6/2009 | Scherson et al. |
| 2009/0237264 A1 | 9/2009 | Bobey |
| 2009/0254159 A1 | 10/2009 | Stormby |
| 2009/0254160 A1 | 10/2009 | Shawver et al. |
| 2010/0010477 A1 | 1/2010 | Augustine et al. |
| 2010/0030306 A1 | 2/2010 | Edelman et al. |
| 2010/0081975 A1 | 4/2010 | Avitable et al. |
| 2010/0121230 A1 | 5/2010 | Vogel et al. |
| 2010/0137764 A1 | 6/2010 | Eddy |
| 2010/0145421 A1 | 6/2010 | Tomlinson et al. |
| 2010/0150991 A1 | 6/2010 | Bernstein |
| 2010/0179469 A1 | 7/2010 | Hammond et al. |
| 2010/0186436 A1 | 7/2010 | Stormby |
| 2010/0210982 A1 | 8/2010 | Balachandran et al. |
| 2010/0249679 A1 | 9/2010 | Perry et al. |

(56) References Cited

U.S. PATENT DOCUMENTS

| | | |
|---|---|---|
| 2010/0249680 A1 | 9/2010 | Davis |
| 2011/0009785 A1 | 1/2011 | Meyer et al. |
| 2011/0034861 A1 | 2/2011 | Schaefer |
| 2011/0037002 A1 | 2/2011 | Johnson et al. |
| 2011/0070447 A1 | 3/2011 | Liu et al. |
| 2011/0082401 A1 | 4/2011 | Iker et al. |
| 2011/0087142 A1 | 4/2011 | Ravikumar et al. |
| 2011/0275983 A1 | 11/2011 | Quisenberry et al. |
| 2011/0282269 A1 | 11/2011 | Quisenberry et al. |
| 2012/0041526 A1 | 2/2012 | Stormby |
| 2012/0130457 A1 | 5/2012 | Gammons et al. |
| 2012/0259266 A1 | 10/2012 | Quisenberry |
| 2013/0030331 A1 | 1/2013 | Quisenberry et al. |
| 2013/0191437 A1 | 7/2013 | Itoh |
| 2013/0216627 A1 | 8/2013 | Galbraith et al. |
| 2013/0245508 A1 | 9/2013 | Maxon-Maldonado |
| 2013/0245519 A1 | 9/2013 | Edelman et al. |
| 2013/0253383 A1 | 9/2013 | Maxon-Maldonado |
| 2013/0261512 A1 | 10/2013 | Maxon-Maldonado et al. |
| 2013/0281947 A1 | 10/2013 | Quisenberry |
| 2013/0331767 A1 | 12/2013 | Quisenberry |
| 2014/0012169 A1 | 1/2014 | Wilford et al. |
| 2014/0046410 A1 | 2/2014 | Wyatt |
| 2014/0052054 A1 | 2/2014 | Quisenberry |
| 2014/0236271 A1 | 8/2014 | Fronda et al. |
| 2014/0257175 A1 | 9/2014 | Quisenberry |
| 2014/0316330 A1 | 10/2014 | Fudem et al. |
| 2014/0323949 A1 | 10/2014 | Quisenberry |
| 2015/0133849 A1 | 5/2015 | Quisenberry et al. |
| 2015/0290364 A1 | 10/2015 | Wall et al. |
| 2015/0328042 A1 | 11/2015 | Parish et al. |
| 2016/0030236 A1 | 2/2016 | Parish et al. |
| 2016/0067104 A1 | 3/2016 | Sarangapani et al. |
| 2016/0082238 A1 | 3/2016 | Wells et al. |
| 2016/0317348 A1 | 11/2016 | Banker |
| 2017/0119940 A1 | 5/2017 | Quisenberry |

FOREIGN PATENT DOCUMENTS

| | | |
|---|---|---|
| EP | 0076074 A1 | 4/1983 |
| EP | 0 489 326 | 6/1992 |
| GB | 2373444 A | 9/2002 |
| JP | 2009504246 A | 2/2009 |
| SU | 689674 | 10/1979 |
| WO | WO-1989009583 A2 | 10/1989 |
| WO | WO-93/09727 | 5/1993 |
| WO | WO-93/12708 A2 | 7/1993 |
| WO | WO-1996005873 A1 | 2/1996 |
| WO | WO-9807397 A1 | 2/1998 |
| WO | WO-1998016176 A1 | 4/1998 |
| WO | WO-00/40186 | 7/2000 |
| WO | WO-01/14012 A1 | 3/2001 |
| WO | WO-01/54635 A1 | 8/2001 |
| WO | WO-2004105676 A1 | 12/2004 |
| WO | WO-2005046760 A1 | 5/2005 |
| WO | WO-2007019038 A2 | 2/2007 |
| WO | WO-2008099017 A1 | 8/2008 |
| WO | WO-2010124234 A1 | 10/2010 |
| WO | WO-2012067918 A1 | 5/2012 |

OTHER PUBLICATIONS

U.S. Appl. No. 12/708,422, Balachandran et al.
U.S. Appl. No. 12/871,188, Parish et al.
U.S. Appl. No. 13/107,264, Quisenberry.
U.S. Appl. No. 12/364,434, Quisenberry.
U.S. Appl. No. 13/190,564, Quisenberry et al.
U.S. Appl. No. 29/397,856, Quisenberry.
U.S. Appl. No. 29/400,194, Quisenberry.
U.S. Appl. No. 29/400,202, Quisenberry.
U.S. Appl. No. 29/400,212, Quisenberry.
U.S. Appl. No. 29/402,115, Quisenberry.
U.S. Appl. No. 13/796,139, Quisenberry.
U.S. Appl. No. 13/962,994, Quisenberry.
U.S. Appl. No. 14/062,428, Quisenberry.
U.S. Appl. No. 14/197,324, Quisenberry.
U.S. Appl. No. 15/227,417, filed Aug. 3, 2016, Overton et al.
U.S. Appl. No. 15/370,689, Quisenberry.
Artikis, T., PCT International Preliminary Report on Patentability dated Jul. 29, 2005, (10 pgs.).
Tom Lee, T.Y. et al; "Compact Liquid Cooling System for Small, Moveable Electronic Equipment", IEEE Transactions on Components, Hybrids, and Manufacturing Technology, Oct. 15, 1992, vol. 15, No. 5, pp. 786-793.
Copenheaver, Blaine R., "International Search Report" for PCT/US2007/022148 dated Apr. 2, 2008, 2 pages.
Young, Lee W., "International Search Report" for PCT/US07/08807 dated Mar. 3, 2008, (3 pages).
Mahmoud Karimi Azar Daryany, et al., "Photoinactivation of *Escherichia coli* and *Saccharomyces cerevisiae* Suspended in Phosphate-Buffered Saline-A Using 266- and 355-nm Pulsed Ultraviolet Light", Curr Microbiol, vol. 56, 2008, pp. 423-428.
J. Li, et al., "Enhanced germicidal effects of pulsed UV-LED irradiation on biofilms", Journal of Applied Microbiology, 2010, pp. 1-8.
Cyro/Temp Therapy Systems; Product News Catalogue; Jobst Institute, Inc., 6 pages (Copyright 1982).
Quisenberry, Tony, "U.S. Appl. No. 13/359,210" filed Jan. 26, 2012.
Quisenberry, Tony, "U.S. Appl. No. 29/424,860" filed Jun. 15, 2012.
Quisenberry, Tony, "U.S. Appl. No. 13/456,410" filed Apr. 26, 2012.
Copenheaver, Blaine R., "International Search Report" for PCT/US2012/035096 dated Aug. 7, 2012, 3 pages.
Quisenberry, Tony, "U.S. Appl. No. 13/558,615" filed Jul. 26, 2012.
Copenheaver, Blaine R., "International Search Report" prepared for PCT/US2013/030475 dated May 23, 2013, 3 pages.
Young, Lee W., International Search Report of PCT Application No. PCT/US2014/64805, dated Mar. 13, 2015 (3 pages).
Hair Science Systems LLC, "Hair Science Systems—01 mobile unit—", Hair Saver Chemo Cold Cap, www.hairsciencesystems.com, 2 pages.
"U.S. FDA de novo clearance for the DigniCap® scalp cooling system that reduces hair loss related to chemotherapy for women with breast cancer", www.sysmex-europe.com/company/news-and-events/press-releases, accessed on Jun. 17, 2016, 3 pages.
"DigniLife—Prevention of Chermotherapy-Induced Alopecia", www.sysmex.co.uk/products/oncology/scalp-cooling-system-dignilife, accessed on Jun. 17, 2016, 3 pages.

* cited by examiner

This diagram shows an alternate method to deliver combination NP and O2 treatment with one pump.

WOUND CARE AND INFUSION METHOD AND SYSTEM UTILIZING A THERAPEUTIC AGENT

CROSS-REFERENCE TO RELATED APPLICATIONS

This application is a continuation-in-part of U.S. patent application Ser. No. 14/197,324, filed on Mar. 5, 2014. U.S. patent application Ser. No. 14/197,324 claims priority to, and incorporates by reference for any purpose the entire disclosure of, U.S. Provisional Patent Application No. 61/776,328, filed Mar. 11, 2013. This application incorporates by reference the entire disclosure of patent application Ser. No. 14/197,324, filed on Mar. 5, 2014, U.S. Provisional Patent Application No. 61/776,328, filed Mar. 11, 2013, U.S. patent application Ser. No. 13/359,210, filed Jan. 26, 2012, U.S. patent application Ser. No. 11/975,047, filed Oct. 17, 2007, U.S. patent application Ser. No. 11/801,662, filed May 9, 2007, U.S. patent application Ser. No. 10/894,369, filed Jul. 19, 2004, U.S. Pat. No. 5,097,829, filed Mar. 19, 1990, U.S. Pat. No. 5,989,285, filed Aug. 15, 1996, and U.S. Pat. No. 6,935,409, filed Jun. 8, 1999.

BACKGROUND

Technical Field

The present disclosure relates to a wound care method and system with oxygenation and infusion therapy, and more particularly, but not by way of limitation, to a wound care system configured to supply therapeutic oxygen and below ambient pressure to a wound area.

Description of the Related Art

A well-recognized aspect of patient treatment is wound care. Medical facilities are constantly in need of advanced technology for the cleaning and treatment of all wounds and, in particular, skin wounds. The larger the skin wound, the more serious are the issues of wound closure and infection prevention. The rapidity of the migration over the wound of epithelial and subcutaneous tissue adjacent the wound is thus critical. Devices have been developed and/or technically described which address certain aspects of such wound healing.

The present disclosure provides improvements in wound care by providing multiple wound healing approaches such as, for example, the application of negative pressure over the wound area along with oxygenation of the wound area. By combining an oxygenation modality that is utilized in conjunction, the individual benefits of negative wound pressure and oxygenation treatments can be synergistically enhanced.

SUMMARY

The present disclosure relates to a wound care method and system with oxygenation and infusion therapy, and more particularly, but not by way of limitation, to a wound care system configured to supply therapeutic oxygen and below ambient pressure to a wound area. In one aspect, the present disclosure relates to a wound-care system that includes a first pump fluidly coupled to an oxygen source. An oxygen concentrator is fluidly coupled to the first pump. A humidification system is fluidly coupled to the oxygen concentrator. A wound dressing is fluidly coupled to the humidification system and to an exudate chamber. A negative-pressure tube fluidly is coupled to the exudate chamber. A first valve is disposed between the first pump and the oxygen concentrator. A second valve is disposed between the oxygen concentrator and the wound dressing. A third valve is disposed in the negative-pressure tube. Selective activation of the first pump, the first valve, the second valve, and the third valve facilitates delivery of at least one of individual, sequential, or simultaneous negative-pressure treatment and oxygen-rich fluid treatment to the wound via the wound dressing.

In another aspect, the present disclosure relates to a method for treating a wound. The method includes applying a wound dressing to the wound. The wound dressing is coupled to an oxygen source and a first pump. At least one of a first treatment modality and a second treatment modality is administered to the wound. The first treatment modality includes supplying oxygen-rich fluid from the oxygen source to a humidifier. Humidified oxygen-rich fluid is delivered, via a pressure gradient, to the wound via the wound dressing. The second treatment modality includes applying, via the first pump, negative pressure to the wound via the wound dressing.

BRIEF DESCRIPTION OF THE DRAWINGS

A more complete understanding of the method and apparatus of the present disclosure may be obtained by reference to the following Detailed Description when taken in conjunction with the accompanying Drawings wherein.

DETAILED DESCRIPTION

Various embodiments of the present disclosure will now be described more fully with reference to the accompanying drawings. The disclosure may, however, be embodied in many different forms and should not be construed as limited to the embodiments set forth herein; rather, the embodiments are provided so that this disclosure will be thorough and complete, and will fully convey the scope of the disclosure to those skilled in the art.

Figure 1:
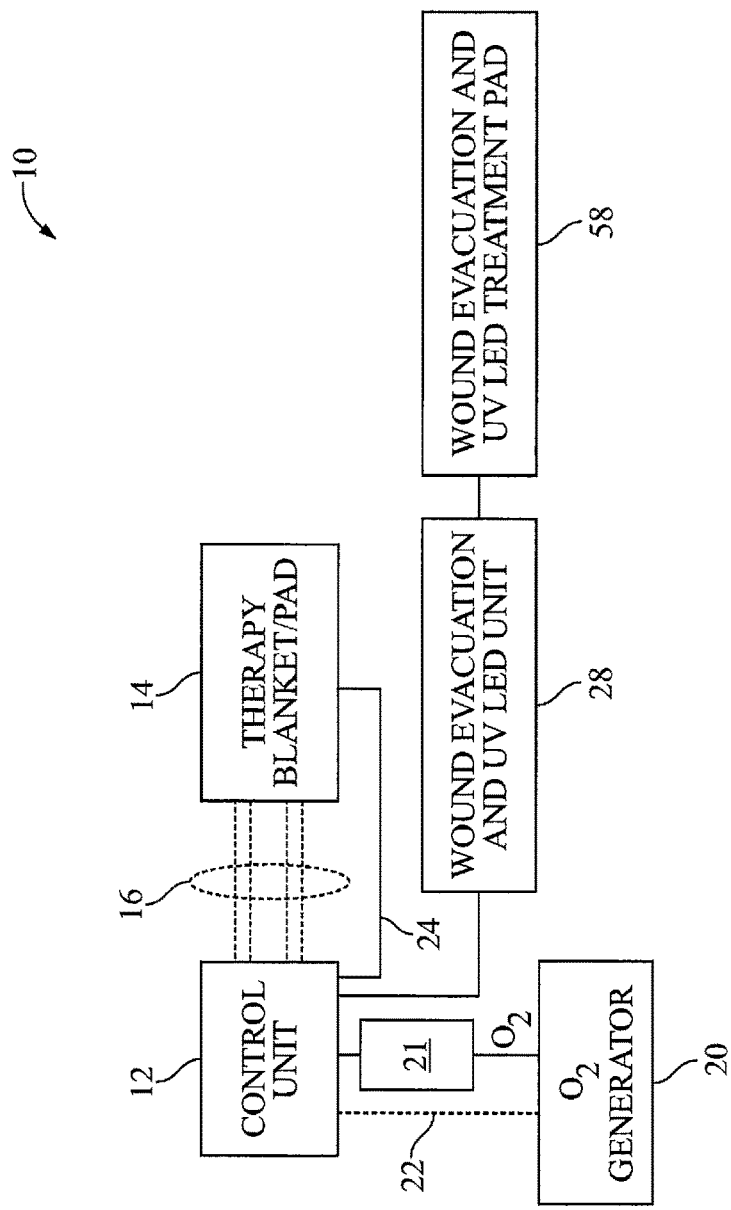
FIG. 1 is an illustration of the wound care system according to an exemplary embodiment.

Referring first to FIG. 1, there is shown an illustration of one embodiment of a wound care system 10 in accordance with principles of the present disclosure. The system 10 comprises a control unit 12, a therapy blanket/pad 14 and a plurality of tubular members 16 (to be defined below) connecting the control unit 12 to the therapy blanket/pad 14. In various embodiments, the system 10 may also include a wound evacuation and ultra violet light emitting diode (UV LED) unit 28 and a wound evacuation and UV LED treatment pad 58. The wound evacuation and UV LED unit 28 is connected to the control unit 12 while the wound evacuation and UV LED treatment pad 58 is connected to the wound evacuation and UV LED unit 28.

Still referring to FIG. 1, the use of the therapy blanket/pad 14 to the wound site of the patient may be, in one embodiment, subsequent to the cleaning of the wound area of dead tissue by the wound evacuation and, in some embodiments, the UV LED treatment pad 58. In one embodiment, Velcro cross straps may be utilized to secure the therapy blanket/pad 14. A 93% concentration of oxygen has been suggested to be advantageous when applied to a wound site as described herein with one or two atmospheres of pressure. In accordance with one aspect of the present disclosure, an oxygen generator/concentrator 20 may be utilized within the control unit 12 or may be separate therefrom. In FIG. 1, an oxygen generator/concentrator 20 is shown in association with the control unit 12 by dotted line 22 and an oxygenation gas line 24 shown extending between the control unit 12 and the therapy blanket/pad 14 as a diagrammatic illustration according to an embodiment of the present disclosure. A humidifier 21 is disposed between the oxygen generator/concentrator 20 and the control unit 12. In a typical embodiment, the humidifier 21 may be, for example, a bubbler, a proton-exchange membrane, or any other type of humidifying device as dictated by design requirements. In a typical embodiment, the humidifier 21 facilitates delivery of oxygen that is humidified above ambient humidity to the wound site. In a typical embodiment, the oxygen delivery is at a partial pressure of approximately 22 mmHg.

In FIG. 1, fiber optic strands (not explicitly shown) direct ultraviolet light from a plurality of LEDs (not explicitly shown) to an array of fiber optic strand ends (not explicitly shown) located on the undersurface of wound evacuation and UV LED treatment pad 58. The control unit 12 may be used to modulate the ultraviolet light to create various patterns of light, different intensities of light, and different durations of light. For example, the control unit 12 may be used to generate pulsed emission of ultraviolet light. The ultraviolet light is capable of penetrating through several layers of skin to destroy infectious bacteria. In one embodiment, not specifically shown herein, the UV LED treatment pad 58 may be provided on the therapy blanket/pad 14. According to exemplary embodiments, the ultraviolet light from the plurality of LEDs located on the undersurface of wound evacuation and UV LED treatment pad 58 destroys a wide variety of microorganisms such as, for example, bacteria which causes skin infections. In addition, the ultraviolet light from the plurality of LEDs improves wound healing along with cell and bone growth. Furthermore, the use of LEDs in light therapy is safe, non-invasive, drug-free and therapeutic.

Figure 2:
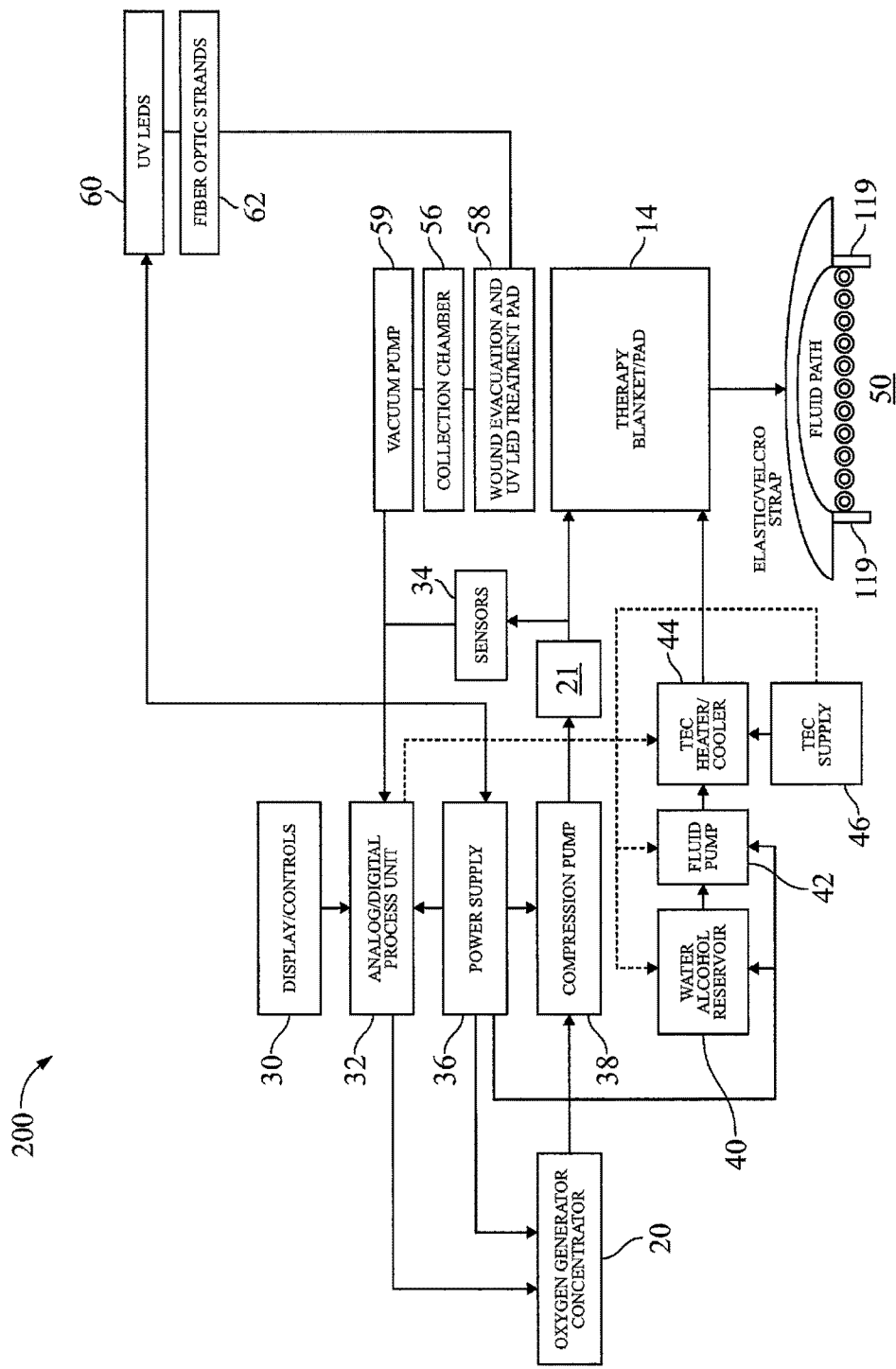
FIG. 2 is a block diagram according to an exemplary embodiment.

Referring now to FIG. 2, there is a block diagram 200 illustrating the flow of oxygenation gas as a transfer fluid according to an embodiment of the present disclosure. As set forth in the block diagram 200, a control unit display 30 is provided in conjunction with an analog/digital processing unit 32. A plurality of sensors 34 are, in various embodiments, utilized in conjunction with the processing unit 32 for control of transfer fluids to the therapy blanket/pad 14 as well as the oxygen delivery thereto. The oxygen generator/concentrator 20 is connected to a power supply 36, which power supply 36, also powers the processing unit 32. The oxygen generated from the oxygen generator/concentrator 20 is then pumped through compression pump 38 and the humidifier 21 before delivery to the therapy blanket/pad 14. It should be noted that an oxygen supply may also be used. In a typical embodiment, the humidifier 21 is disposed between the oxygen generator/concentrator 20 and the therapy blanket/pad 14. In the embodiment shown in FIG. 2, the humidifier 21 is disposed between the compression pump 28 and the therapy blanket/pad 14; however, in other embodiments, the humidifier 21 may be disposed between the oxygen generator/concentrator 20 and the compression pump 38. In a typical embodiment, the humidifier 21 facilitates delivery of oxygen that is humidified above ambient humidity to the wound site. In a typical embodiment, the oxygen delivery is at a partial pressure of approximately 22 mmHg.

Referring still to FIG. 2, a water/alcohol reservoir 40 is shown in fluid flow communication with fluid pump 42 and, in various embodiments, a Thermo Electric Cooler (TEC) heater/cooler 44. The TEC heater/cooler 44 may be controlled by the processing unit 32 and a TEC supply 46 is likewise shown. Adjacent the TEC supply 46 is illustrated a diagrammatical schematic of a treatment chamber 50 defined beneath the therapy blanket/pad 14 wherein the treatment chamber 50 is thermally exposed to the thermal fluid by the fluid path therein illustrated. The adhesive attachment edges 52 therein shown likewise define the treatment chamber space 50 between the therapy blanket/pad 14 and the wound site to allow for the flow of the oxygenation gas therein.

Referring still to FIG. 2, there is shown a negative-pressure pump 59 powered by the power supply 36. A collection chamber 56 is connected to the negative-pressure pump 59 and to a wound evacuation and UV LED treatment pad 58. The wound evacuation and UV LED treatment pad 58 is used prior to the therapy blanket/pad 14, in one embodiment of the present disclosure, for cleaning the wound area in preparation for oxygenation in conjunction with thermal therapy in accordance with the present disclosure.

Referring still to FIG. 2, there is shown a plurality of ultraviolet LEDs 60 and fiber optic strands 62, which are interoperably connected to the wound evacuation and UV LED treatment pad 58. The wound evacuation and UV LED treatment pad 58 is used prior to the therapy blanket/pad 14, in one embodiment of the present disclosure, for removing bacteria from the wound area in preparation for oxygenation in accordance with an embodiment. According to exemplary embodiments, ultraviolet light from the plurality of LEDs 60 destroys a wide variety of microorganisms such as, for example, bacteria which causes skin infections. In addition, the ultraviolet light from the plurality of LEDs 60 improves wound healing along with cell and bone growth. Furthermore, the use of the plurality of LEDs 60 in light therapy is safe, non-invasive, drug-free and therapeutic.

According to exemplary embodiments, the ultraviolet light from the plurality of LEDs 60 is in the range of approximately 200 to 450 nanometers and higher, and energy levels of up to 35,000 microwatt seconds/cm$^2$, which are necessary to eliminate or destroy most microorganisms such as bacteria, spores, algae and viruses. Most bacteria can be destroyed at ultra violet energies of from about 3,000 to about 5,000 microwatt-seconds/cm$^2$ while mold spores may require energies in the 20,000 to 35,000 mW-seconds/cm$^2$.

Figure 3:
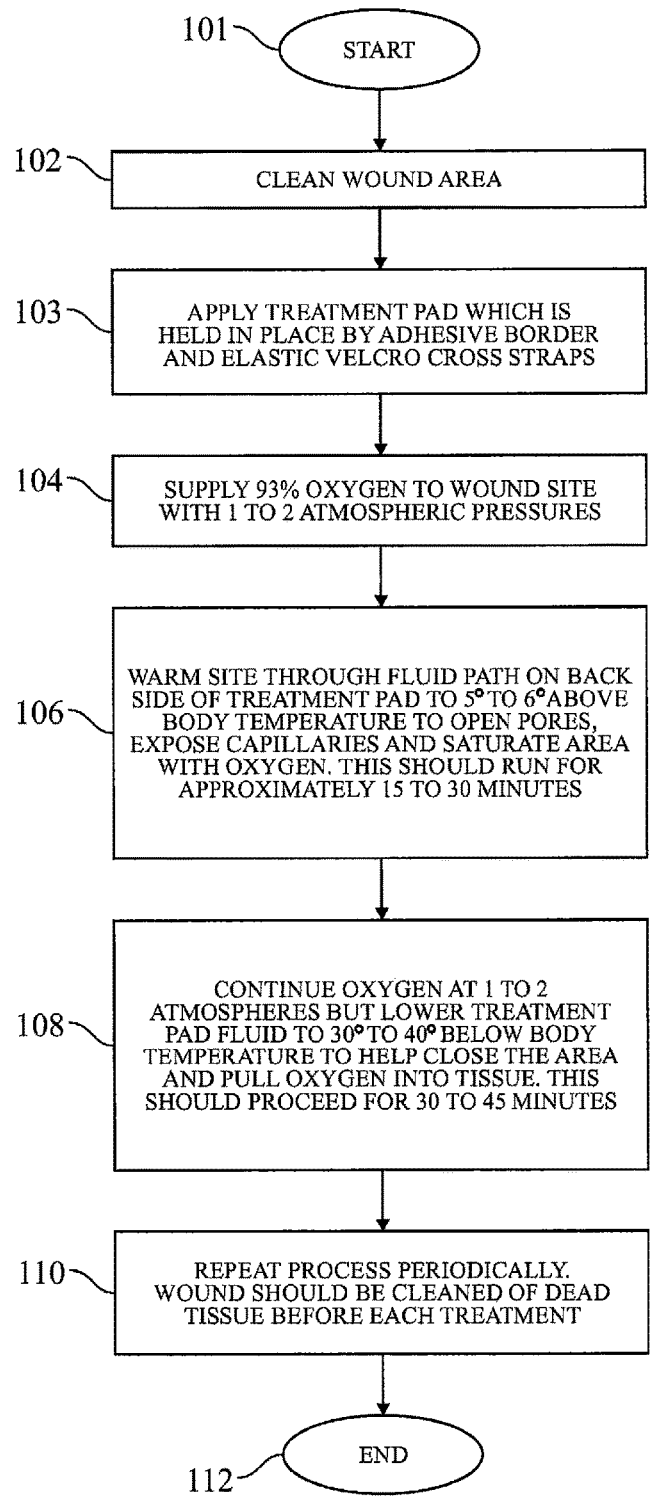
FIG. 3 is a flow diagram of a process according to an exemplary embodiment.

Referring now to FIG. 3 there is shown a flow diagram of a process 300 according to an embodiment. The process 300 starts at step 101. At step 102, the wound area is cleaned of dead tissue, any undesirable fluids, and bacteria by applying the wound evacuation and UV LED treatment pad 58. The wound evacuation and UV LED treatment pad 58 is used prior to the therapy blanket/pad 14 for removing bacteria from the wound area in preparation for oxygenation in accordance with the present disclosure. According to exemplary embodiments, the ultraviolet light from the plurality of LEDs located on the undersurface of wound evacuation and UV LED treatment pad 58 destroys a wide variety of microorganisms such as, for example, bacteria which causes skin infections. In addition, the ultraviolet light from the plurality of LEDs improves wound healing along with cell and bone growth. Furthermore, the use of LEDs in light therapy is safe, non-invasive, drug-free and therapeutic.

At step 103, the therapy blanket/pad 14 is applied to the wound area. The therapy blanket/pad 14 is held in position by an adhesive border and, in one embodiment, elastic Velcro cross straps. At step 104, according to an embodiment, an oxygenation gas comprising on the order of 93% concentration of oxygen gas is delivered to the wound site with one to two atmospheric pressures. The numbers as set forth and shown are exemplary and other oxygenation concentrations as well as pressures are contemplated in various embodiments. In a typical embodiment, the humidifier 21 facilitates delivery of oxygen that is humidified above ambient humidity to the wound site. In a typical embodiment, the oxygen delivery is at a partial pressure of approximately 22 mmHg.

In step 106, the site is warmed through the fluid path herein shown on the back side of the therapy blanket/pad 14 up to approximately 5 to approximately 6 degrees above the body temperature of the patient. Warming allows the pores of the patient's skin to open, exposing capillaries therein. The capillaries of the skin are then saturated with oxygen. In one period of time herein described, a warming period of approximately 15 to approximately 30 minutes is recommended. At step 108, oxygenation is continued at one to two atmospheres and the therapy blanket/pad fluid is lowered to approximately 30 to approximately 40 degrees below body temperatures. Cooling closes the pores of the wound area and pulls oxygen into the underlying tissue. Cooling then proceeds for approximately 30 to approximately 45 minutes in accordance with an embodiment. At step 110, the process 300 may be repeated periodically and the wound area may be cleaned of dead tissue before each treatment. At step 112, the process 300 ends.

Figure 4:
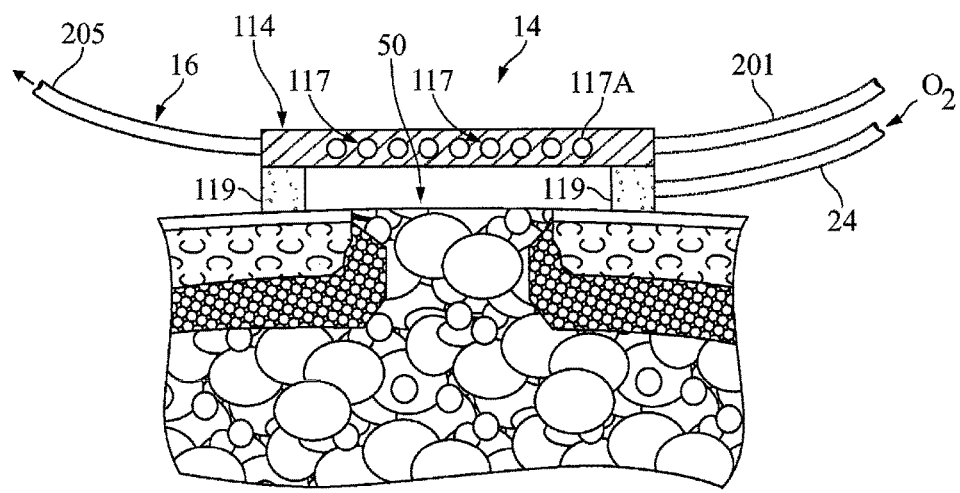
FIG. 4 illustrates a side elevational cross sectional view of a therapy blanket/pad according to an exemplary embodiment.

FIG. 4 is a side elevational, cross sectional view of one embodiment of the therapy blanket/pad 14. In an embodiment, the therapy blanket/pad 14 is constructed with a single bladder 114 where, in various embodiments, thermal fluid flow may be provided. The tubular members 16 are coupled to the therapy blanket/pad 14. The therapy blanket/pad is fabricated with a circuitous flow path therein for thermal fluid flow. The circuitous flow path may be tubular in form, or simply a path within therapy blanket/pad 14 defined by flow channels. What is shown is a path 117 within therapy blanket/pad 14. The path 117 is shown with tubular ends 117A, for example, illustrating that thermal fluid flows therein for thermal treatment of the underlying wound area. Again, the path 117 may not be of tubular form and may have a variety of shapes and fabrication techniques well known in the art of therapy pads.

According to an exemplary embodiment, the therapy blanket/pad 14 is separated from the patient's skin by adhesive strips 119 having a thickness of, for example, ⅛ inch. The therapy blanket/pad 14 (not drawn to scale) injects humidified oxygen into the treatment chamber 50. The injection of humidified oxygen helps treat the wound area and any stasis zones therein where tissue swelling has restricted flow of blood to tissues within the wound area. It is well known that, without sufficient blood flow, the epithelial and subcutaneous tissues referenced above receive less oxygen and are less able to migrate over the wound area to promote healing. By utilizing the embodiments disclosed herein, oxygenation is enhanced and the problems associated with such conditions are mitigated.

Figure 5:
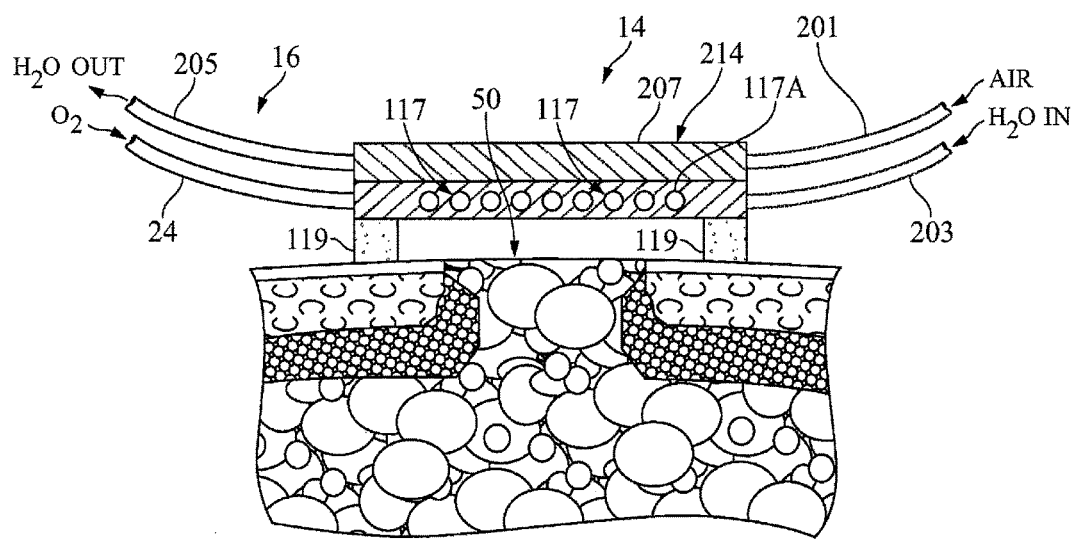
FIG. 5 illustrates a side elevational cross sectional view of a therapy blanket/pad according to an exemplary embodiment.

FIG. 5 illustrates an exemplary embodiment of the therapy and oxygenation treatment pad of FIG. 4. A dual bladder 214 is thus provided where air may be applied to second bladder 207 atop the path 117, also represented by the "tubular" ends 117A shown for purposes of example only. In this manner, select compression therapy may be afforded in conjunction with the oxygenation treatment. In that regard, air inlet tube 201 is connected to the second bladder 207. Both FIGS. 4 and 5 show oxygen tube 24 for feeding humidified oxygen to the treatment chamber 50, with tube 203, which in some embodiments, allows thermal fluid into conduits 117 with tube 205 allowing thermal fluid return to control unit 12 of FIG. 1. FIG. 5 further illustrates the advantages of FIG. 4 with the ability for either compression or sequenced compression as referenced above.

Figure 6:
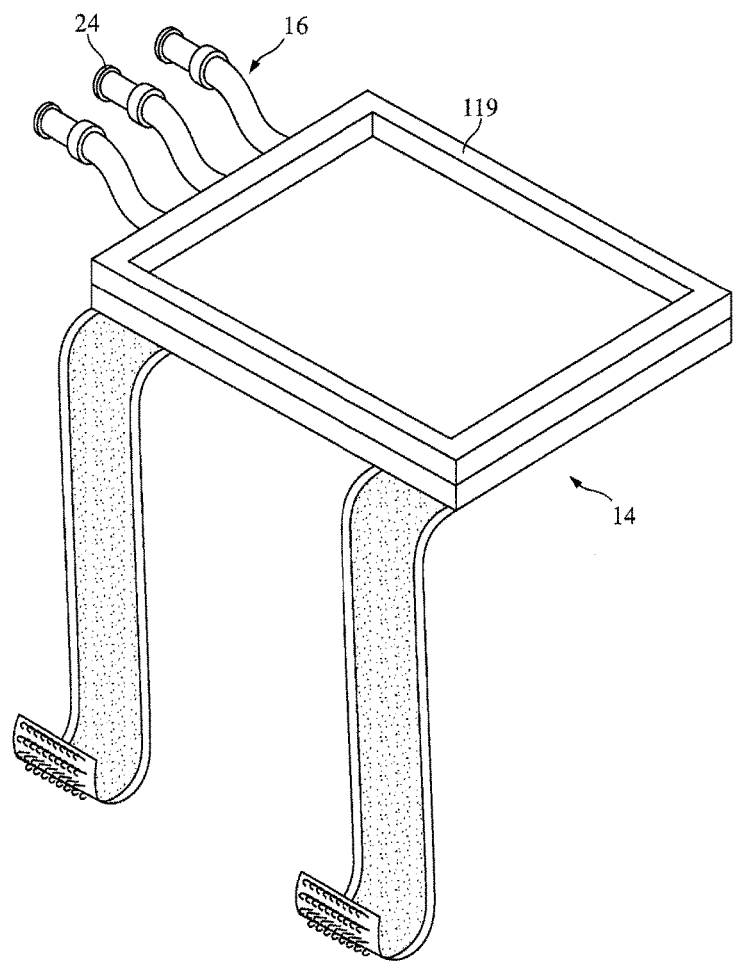
FIG. 6 is a diagrammatic illustration of a therapy blanket/pad according to an exemplary embodiment.

Referring now to FIG. 6, there is shown a diagrammatic illustration of the therapy blanket/pad 14 of FIGS. 1 and 4. The tubular members 16 for, in some embodiments, thermal fluid flow and the tube 24 for humidified oxygen flow are clearly seen. The adhesive border 119 is likewise shown.

Figure 7:
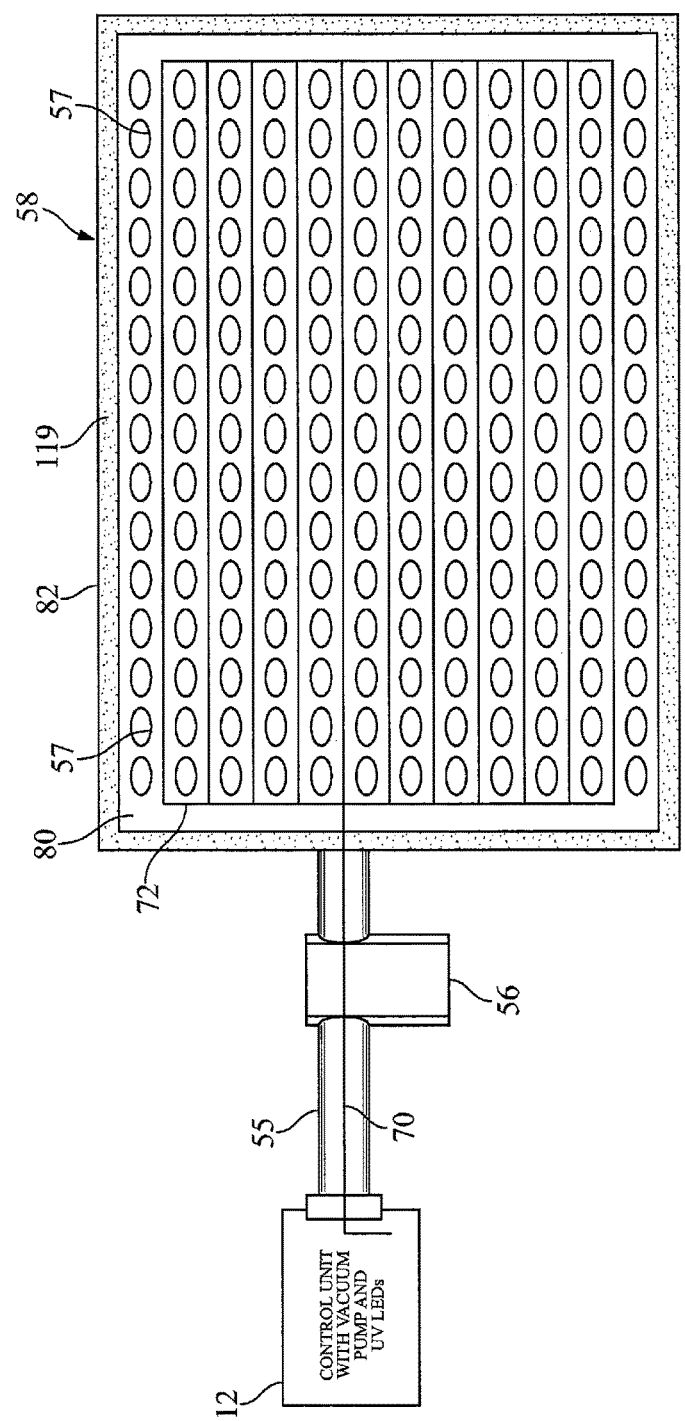
FIG. 7 is a diagrammatic illustration of a wound evacuation and UV LED treatment pad according to an exemplary embodiment.

FIG. 7 is diagrammatic illustration of a wound evacuation and UV LED treatment pad 58 according to an embodiment of the present disclosure. In this embodiment, the wound evacuation and UV LED treatment pad 58 contains an array of fiber optic strand 72 to project ultraviolet light onto a wound area (not explicitly shown). In a typical embodiment, the fiber optic strands 72 may be cleaved side emitting fibers. The wound evacuation and UV LED treatment pad 58 also contains an array of unique removal ports 57 that may be used to remove any undesirable fluid from the wound area. The wound evacuation and UV LED treatment pad 58 further contains a non-tissue adhesive service 80 which contains both the fiber optic strand array 72 and the unique removal ports 57. An adhesive circumference 82 is located around the periphery of the wound evacuation and UV LED treatment pad 58 to allow for a seal to be formed around the wound area. The seal, in conjunction with the removal ports 57, allows a negative pressure to form over the wound area. Negative pressure facilitates removal undesirable tissues from the wound area. The wound evacuation and UV LED treatment pad 58 is connected to a control unit 12. The control unit 12 contains a negative-pressure pump (not shown) and a plurality of ultraviolet LEDs (not explicitly shown). The negative-pressure pump is connected to the wound evacuation and UV LED treatment pad 58 via a negative-pressure line 55. A collection chamber 56 is positioned between the negative-pressure pump and the wound evacuation and UV LED treatment pad 58 to intercept and store undesirable fluids, tissues, and the like that are removed from the wound area as a result of negative pressure applied to the wound area with the negative-pressure pump. The plurality of ultraviolet LEDs transmit ultraviolet light through the fiber optic strands 70 to the wound evacuation and UV LED treatment pad 58, where the fiber optic strands 70 are then dispersed throughout the wound evacuation and UV LED treatment pad 58 to project ultraviolet light onto the wound area. Energy delivered by the plurality of LEDs enhances cellular metabolism, accelerates repair and replenishment of damaged skin cells, as well as stimulates production of collagen which is the foundation of a healthy and smooth skin. Light therapy is non-ablative, non-invasive, and painless.

Figure 8A:
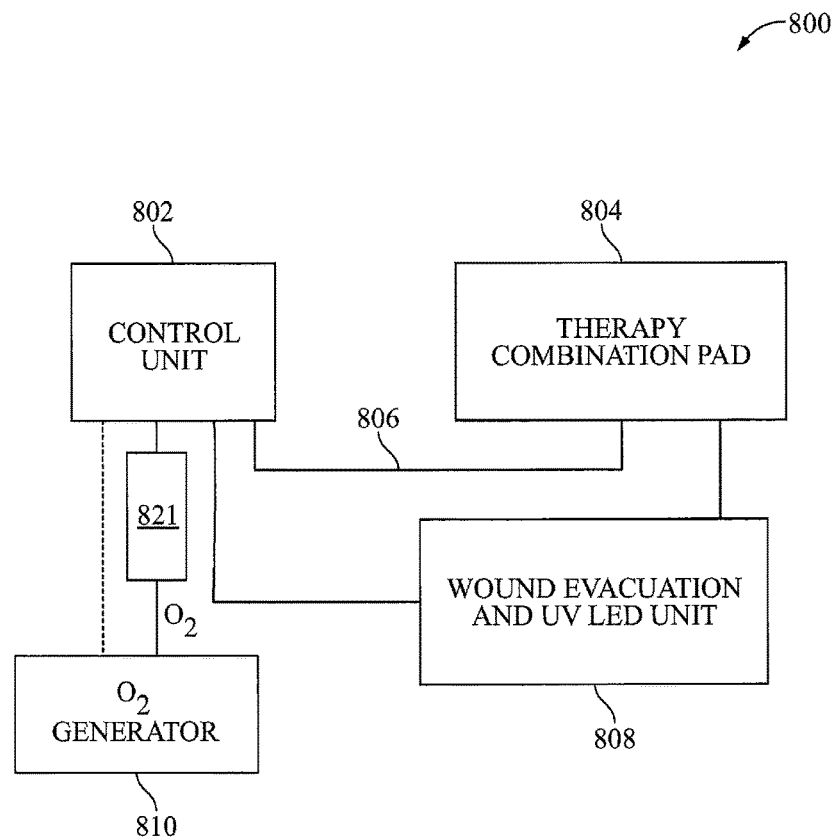
FIG. 8A is a schematic diagram of a wound care system according to an exemplary embodiment.

FIG. 8A is a schematic diagram of a wound care system according to an exemplary embodiment. A wound care system 800 includes a control unit 802, a combination therapy pad 804, and a plurality of tubular members 806 connecting the combination therapy pad 804 to the control unit 802. A wound evacuation and UV-LED unit 808 is associated with the control unit 802 and connected to the combination therapy pad 804. In various embodiments, the wound evacuation and UV-LED unit 808 and the control unit 802 are contained in a single housing; however, in various alternative embodiments, the wound evacuation and UV-LED unit 808 and the control unit 802 may not be in a single housing and are independent devices.

Still referring to FIG. 8A, use of the combination therapy pad 804 incorporates evacuation therapy for wound cleaning with oxygenation therapy known to promote healing. In various embodiments, Velcro cross straps are used to secure the combination therapy pad 804. An oxygen generator/concentrator 810 is utilized to provide, for example, a 93% concentration of oxygen to a wound site via the combination therapy pad 804. In a typical embodiment, the oxygen generator/concentrator 810 and the control unit 802 are separate devices; however, in other embodiments, the oxygen generator/concentrator 810 and the control unit 802 are contained in a single housing. A humidifier 821 is disposed between the oxygen generator/concentrator 810 and the control unit 802. In a typical embodiment, the humidifier 821 may be, for example, a bubbler, a proton-exchange membrane, or any other type of humidifying device as dictated by design requirements. In a typical embodiment, the humidifier 821 facilitates delivery of oxygen that is humidified above ambient humidity to the wound site. In a typical embodiment, the oxygen delivery is at a partial pressure of approximately 22 mmHg.

Still referring to FIG. 8A, fiber optic strands (not explicitly shown) direct ultraviolet light from a plurality of LEDs (not explicitly shown) located in the wound evacuation and UV-LED unit 808 to an array of fiber optic strands (not explicitly shown) located on an undersurface of the combination therapy pad 804. The control unit 802 may be used to modulate the ultraviolet light to create, for example, various patterns of light, different intensities of light, and different durations of light. For example, in various embodiments, the control unit 802 is used to produce pulsed emission of the ultraviolet light.

Figure 8B:
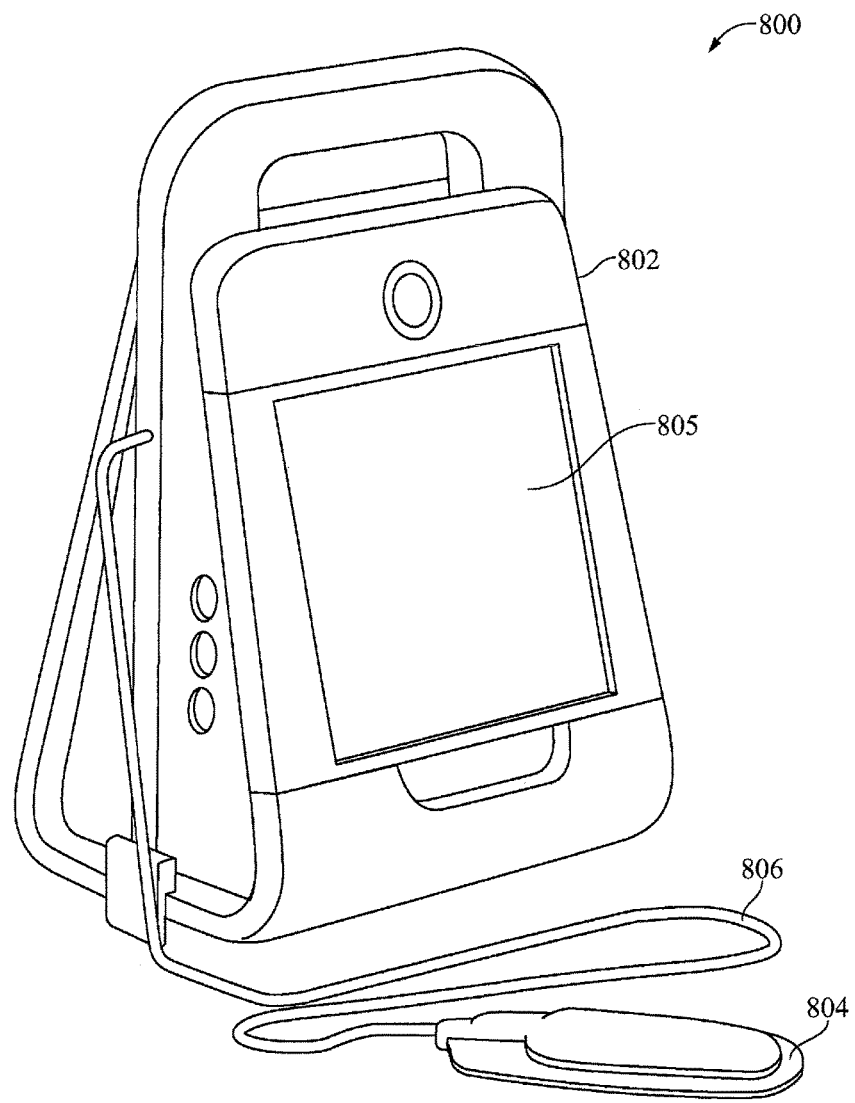
FIG. 8B is a front perspective view of a wound care system according to an exemplary embodiment.

FIG. 8B is a front perspective view of a wound care system according to an exemplary embodiment. The wound care system 800 includes the control unit 802, the combination therapy pad 804, and the plurality of tubular members 806 connecting the combination therapy pad 804 to the control unit 802. A user interface 805 is disposed on a front surface of the control unit 802. In a typical embodiment, the user interface 805 allows a user to control various parameters of wound care-treatment including, for example, oxygen concentration, oxygen pressure and, if applicable, temperature, and ultra-violet light intensity. The user interface 805 may be pivoted relative to the control unit 802 to provide a favorable viewing angle. In a typical embodiment, the user interface 805 may be, for example a touch screen interface; however, in other embodiments, the user interface 805 may be, for example, a plurality of controls or any other user interface. In various embodiments, Velcro cross straps (not shown) may be used to secure the combination therapy pad 804.

Figure 8C:
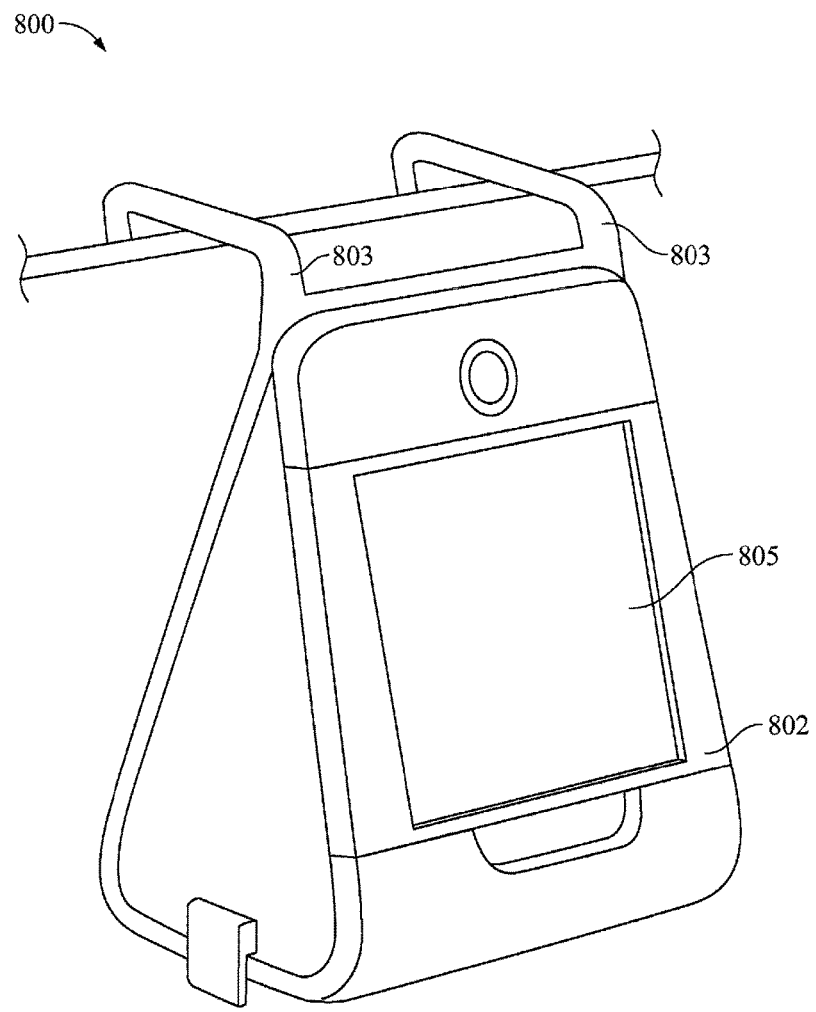
FIG. 8C is a front perspective view of a wound care system illustrating a plurality of hooks according to an exemplary embodiment.

FIG. 8C is a front perspective view of the wound care system of FIG. 8A illustrating a plurality of foldable hooks. The wound care system 800 includes a plurality of foldable hooks 803 disposed, for example, along a top of the control unit 802. In a typical embodiment, the plurality of foldable hooks 803 may be utilized to hang the control unit 802 from, for example, a hospital bed.

Figure 9:
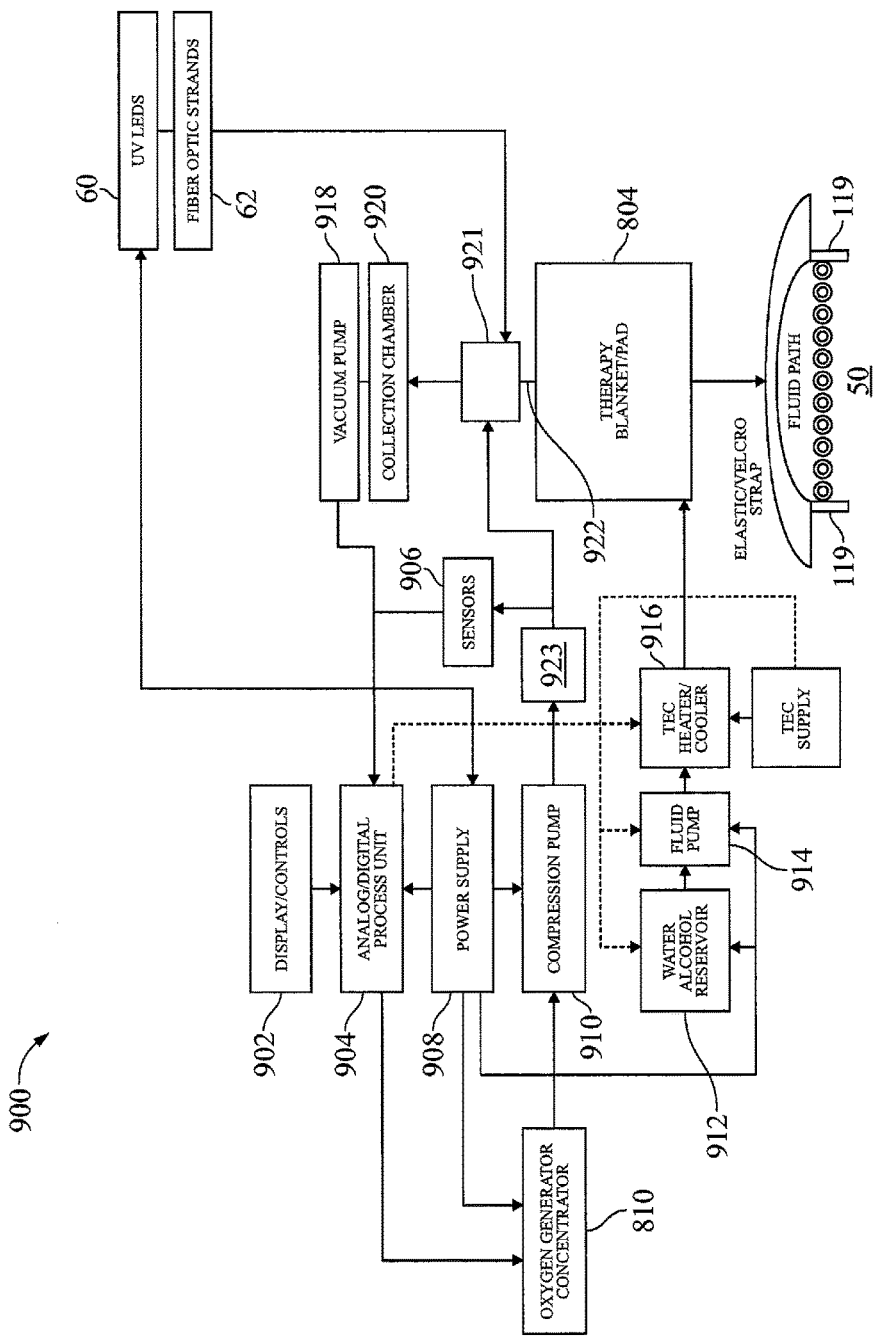
FIG. 9 is a is a block diagram of a wound care system according to an exemplary embodiment.

FIG. 9 is a block diagram of a wound care system according to an exemplary embodiment. In a wound-care system 900, a control unit display 902 is provided in conjunction with a processing unit 904. In a typical embodiment, the processing unit 904 is an analog/digital processing unit. In various embodiments, a plurality of sensors 906 may be utilized in conjunction with the processing unit 904 for control of heat transfer fluids to a combination therapy pad 804. In various embodiments, the oxygen generator/concentrator 810 is connected to a power supply 908. The power supply 908 also powers the processing unit 904. Oxygen generated by the oxygen generator/concentrator 810 is pumped through a compression pump 910, a humidifier 923, and a pressure switch 921 before being delivered to the combination therapy pad 804. In a typical embodiment, the humidifier 923 is disposed between the oxygen generator/ concentrator 810 and the therapy blanket/pad 804. In the embodiment shown in FIG. 9, the humidifier 923 is disposed between the compression pump 910 and the therapy blanket/pad 804; however, in other embodiments, the humidifier 923 may be disposed between the oxygen generator/concentrator 810 and the compression pump 910. In a typical embodiment, the humidifier 923 facilitates delivery of oxygen that is humidified above ambient humidity to the wound site. In a typical embodiment, the oxygen delivery is at a partial pressure of approximately 22 mmHg.

Still referring to FIG. 9, in various embodiment, a water/alcohol reservoir 912 may be in fluid communication with a fluid pump 914 and a thermoelectric cooler 916. The thermoelectric cooler 916 is controlled by the processing unit 904. In a typical embodiment, a negative-pressure pump 918 is powered by the power supply 908. A collection chamber 920 is fluidly connected to the negative-pressure pump 918 and the pressure switch 921. The pressure switch 921 is fluidly coupled to the combination therapy pad 804. In a typical embodiment, oxygen therapy and negative-pressure therapy are each administered to the combination therapy pad 804 through a common port 922. In a typical embodiment, the pressure switch 921 is capable of adjusting the combination therapy pad 804 between negative-pressure treatment and oxygenation therapy.

Figure 10:
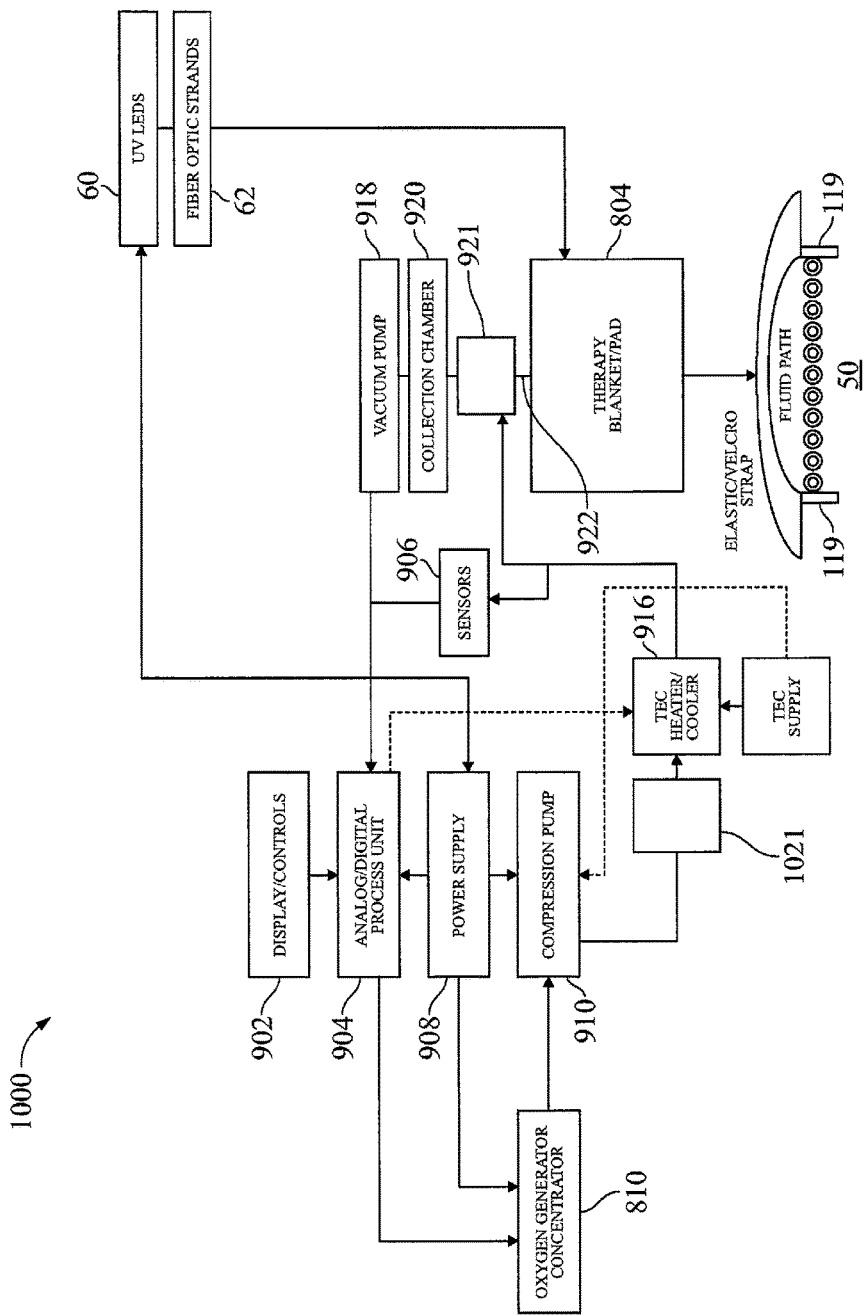
FIG. 10 is a block diagram of a wound care system according to an exemplary embodiment.

FIG. 10 is a block diagram of a wound care system according to an exemplary embodiment. In a typical embodiment, a wound care system 1000 is similar in construction to the arrangement described above with respect to FIG. 9. However, the wound care system 1000 does not include a water/alcohol reservoir or a fluid pump as shown in FIG. 9. In a various embodiment, the thermoelectric cooler 916 may be in fluid communication with the compression pump 910. Thus, thermal therapy may be supplied to the combination therapy pad 804 through heating and cooling of the oxygen supplied by the oxygen generator/concentrator 810. In a typical embodiment, a humidifier 1021 is disposed between the oxygen generator/concentrator 810 and the therapy blanket/pad 804. In the embodiment shown in FIG. 10, the humidifier 1021 is disposed between the compression pump 910 and the therapy blanket/pad 804; however, in other embodiments, the humidifier 1021 may be disposed between the oxygen generator/concentrator 810 and the compression pump 910. In a typical embodiment, the humidifier 1021 facilitates delivery of oxygen that is humidified above ambient humidity to the wound site. In a typical embodiment, the oxygen delivery is at a partial pressure of approximately 22 mmHg.

Figure 11:
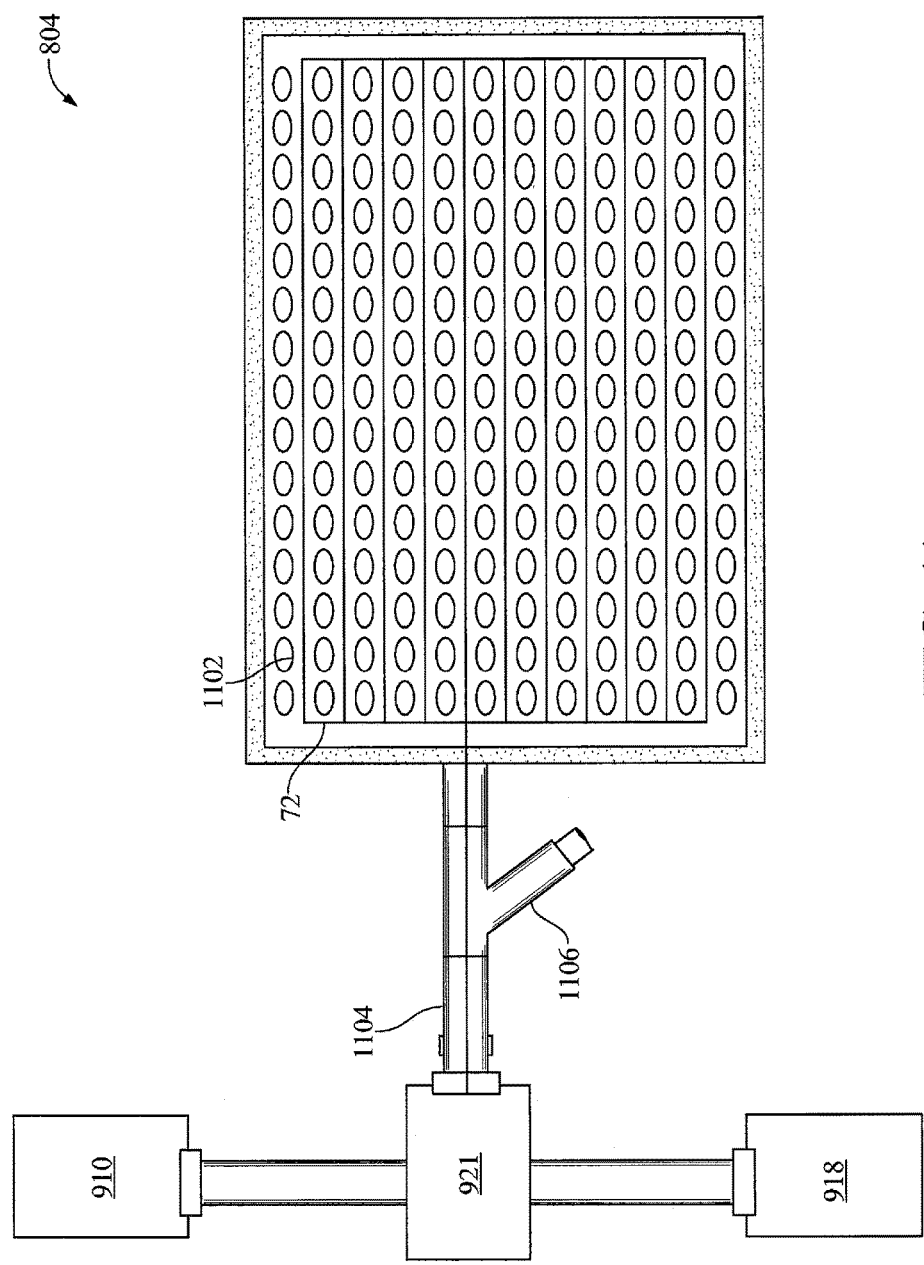
FIG. 11 is a diagrammatic illustration of a combination therapy pad according to an exemplary embodiment.

FIG. 11 is a diagrammatic illustration of a combination therapy pad according to an exemplary embodiment. In a typical embodiment, the combination therapy pad 804 includes a plurality of fiber optic strands 72 to project ultraviolet light onto a wound area (not explicitly shown). In various embodiments, the fiber optic strands 72 may be cleaved or side-emitting fibers; however, one skilled in the art will recognize that any type of fiber-optic strand could be used. In a typical embodiment, the combination therapy pad 804 also includes a plurality of oxygenation/removal ports 1102. In a typical embodiment, the oxygenation/removal ports 1102 alternate between providing oxygen therapy and negative-pressure therapy to the wound area.

Still referring to FIG. 11, in a typical embodiment, oxygen therapy and negative-pressure therapy is administered to the combination therapy pad 804 via an evacuation/oxygenation line 1104. The evacuation/oxygenation line 1104 is fluidly coupled to the pressure switch 921. The pressure switch 921 is fluidly connected to the compression pump 910 and the negative-pressure pump 918. Thus, in a typical embodiment, the pressure switch 921 is capable of adjusting the combination therapy pad 804 between negative-pressure treatment and oxygenation therapy.

Still referring to FIG. 11, in various embodiments, a luer lock 1106 is fluidly coupled to the combination therapy pad 804. During treatment, it is often necessary to administer various medications to a wound site. Such administration often requires removal of a wound dressing such as, for example, the combination therapy pad 804. Frequent removal of the wound dressing can increase risk of further damage to tissue immediately surrounding the wound site. In a typical embodiment, the luer lock 1106 allows for administration of medications and other therapeutic compounds directly to a wound site without the need to remove the combination therapy pad 804.

Figure 12:
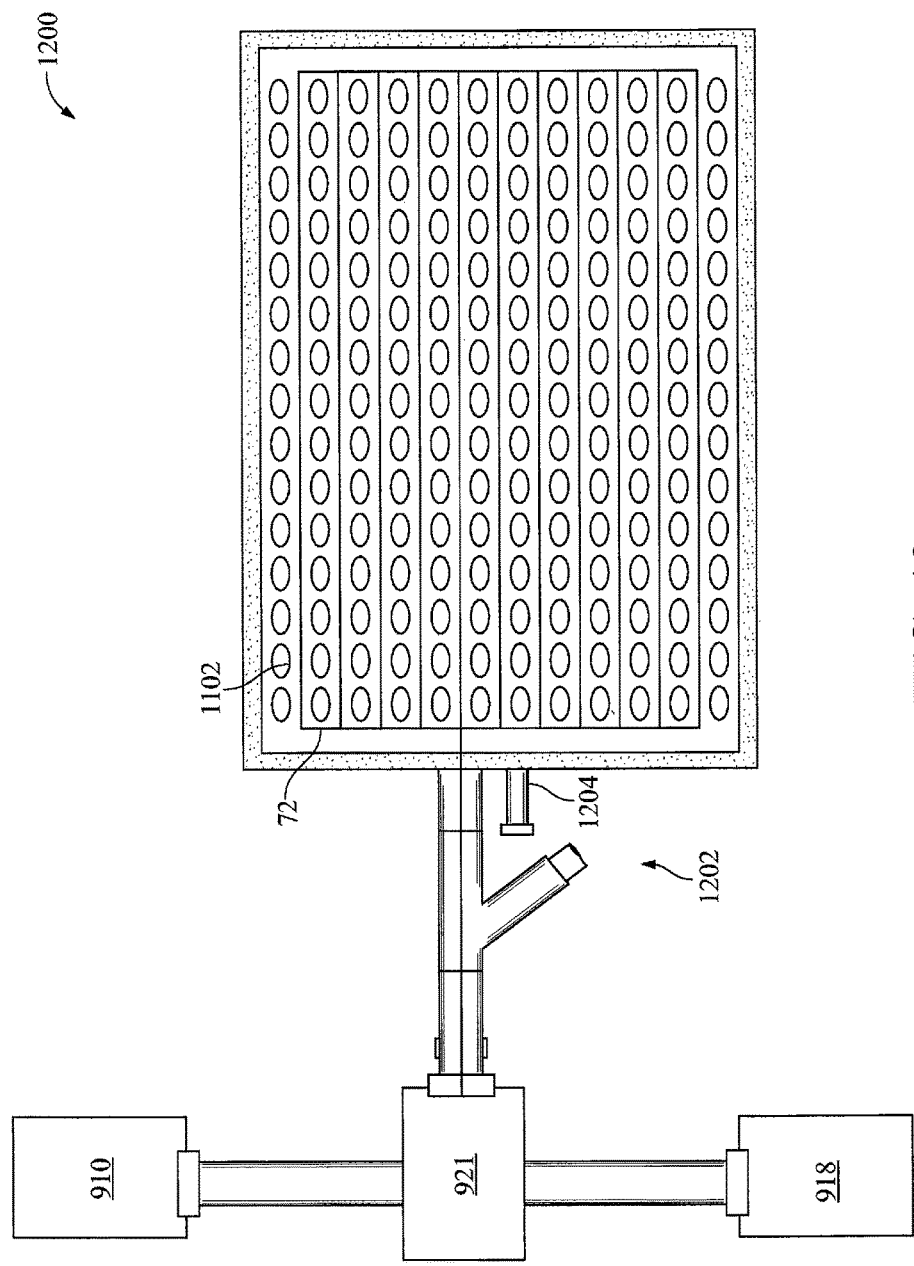
FIG. 12 is a diagrammatic illustration of a combination therapy pad according to an exemplary embodiment.

FIG. 12 is a diagrammatic illustration of a combination therapy pad according to an exemplary embodiment. In a typical embodiment, the combination therapy pad 1200 includes the plurality of fiber optic strands 72 to project ultraviolet light onto a wound area (not explicitly shown). In a typical embodiment, a combination therapy pad 1200 also includes a radio frequency ("RF") antenna 1202. In a typical embodiment, the RF antenna 1202 comprises a wire 1204. The wire 1204 extends along a length of the combination therapy pad 1204. In a typical embodiment, the wire 1204 is disposed within the combination therapy pad 1200 so that, during use, the wire is in close proximity to a wound area. In various embodiments, the wire 1204 is insulated to reduce risk of electric shock to a patient.

Figure 13:
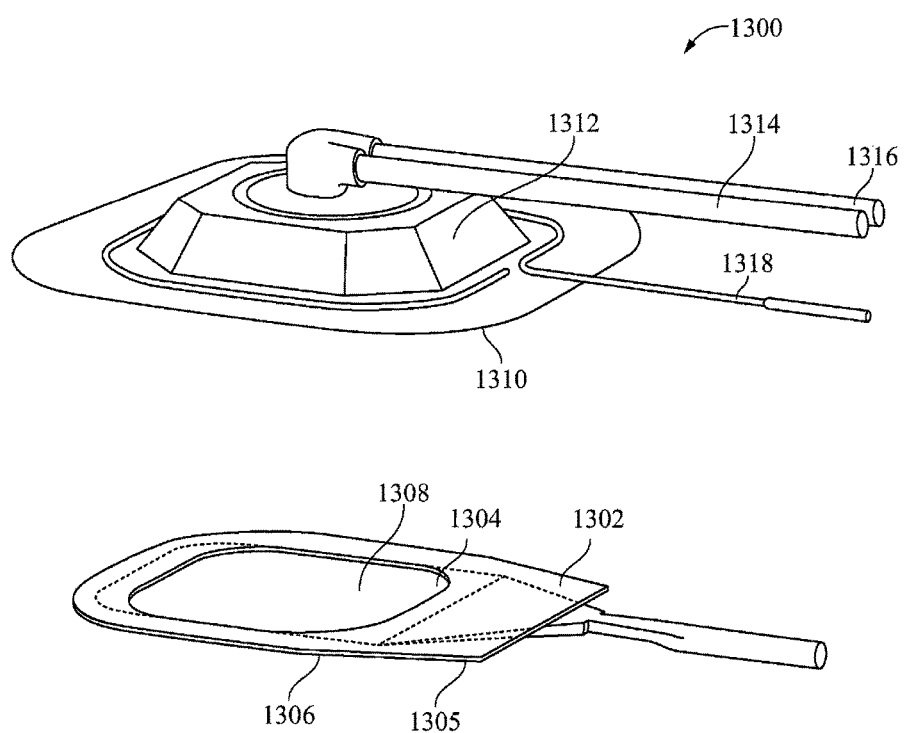
FIG. 13 is an exploded view of a combination therapy pad according to an exemplary embodiment.

FIG. 13 is an exploded view of a combination therapy pad according to an exemplary embodiment. A combination therapy pad 1300 includes a first layer 1302 having a first central gap 1304 formed therein. In a typical embodiment, the first layer 1302 is constructed of, for example, urethane. A second layer 1305 is disposed below the first layer 1302 and includes an adhesive bottom surface 1306. A second central gap (not explicitly shown) is formed in the second layer 1305 In a typical embodiment, the second layer 1305 is constructed of, for example, urethane. The first layer 1302 and the second layer 1305 are coupled to each other around a perimeter of the first layer 1302 and the second layer 1305 so that the second central gap aligns with the first central gap 1304. A fiber-optic array 1308 is disposed between the first layer 1302 and the second layer 1305 so as to fill a space defined by the first central gap 1304 and the second central gap.

Still referring to FIG. 13, a third layer 1310 is disposed above the first layer 1302. The third layer 1310 includes a recessed central area 1312. The recessed central area 1312 is fluidly coupled to a negative-pressure tube 1314 via a first port and a therapeutic fluid tube 1316 via a second port. An antenna 1318 is coupled to the third layer 1310. The antenna 1318 is formed into a loop and is generally arranged around a perimeter of the recessed central area 1312. In a typical embodiment, the first layer 1302, the second layer 1305, and the third layer 1310 are coupled to each other via a process such as, for example, adhesive bonding or welding.

Still referring to FIG. 13, during operation, the adhesive bottom surface 1306 is placed on a bodily region of a patient proximate a wound area. In a typical embodiment, the adhesive bottom surface 1306 is oriented such that the second central gap is positioned over the wound area. Thus, the adhesive bottom surface 1306 is not in direct contact with the wound area. The fiber-optic array 1308 is disposed over the wound area and, in various embodiments, may contact the wound area. The fiber-optic array 1308 delivers UV lighting to the wound area thereby promoting cleaning and disinfection of the wound area. The negative-pressure tube 1314 applies negative pressure to the wound area thereby removing undesirable fluids, tissues, and the like from the wound area. The therapeutic fluid tube 1316 provides a therapeutic fluid such as, for example, humidified oxygen to the wound area.

Still referring to FIG. 13, during operation, a pulsed radio-frequency ("RF") signal having a pulse frequency on the order of, for example 27 MHz, is transmitted to the antenna 1318. In a typical embodiment, an amplitude of the pulsed RF signal is on the order of, for example, a fraction of a Watt. Such an amplitude is below a threshold where federal licensing is typically required. The antenna 1318 receives the pulsed RF signal from a radio-frequency source and transmits the pulsed RF signal to a region in close proximity to the wound area. Exposing the wound area to the pulsed RF signal has been shown to be beneficial to healing by encouraging intracellular communication. In particular, pulsed RF signals have been shown to stimulate cellular bonding, and metabolism.

Figure 14:
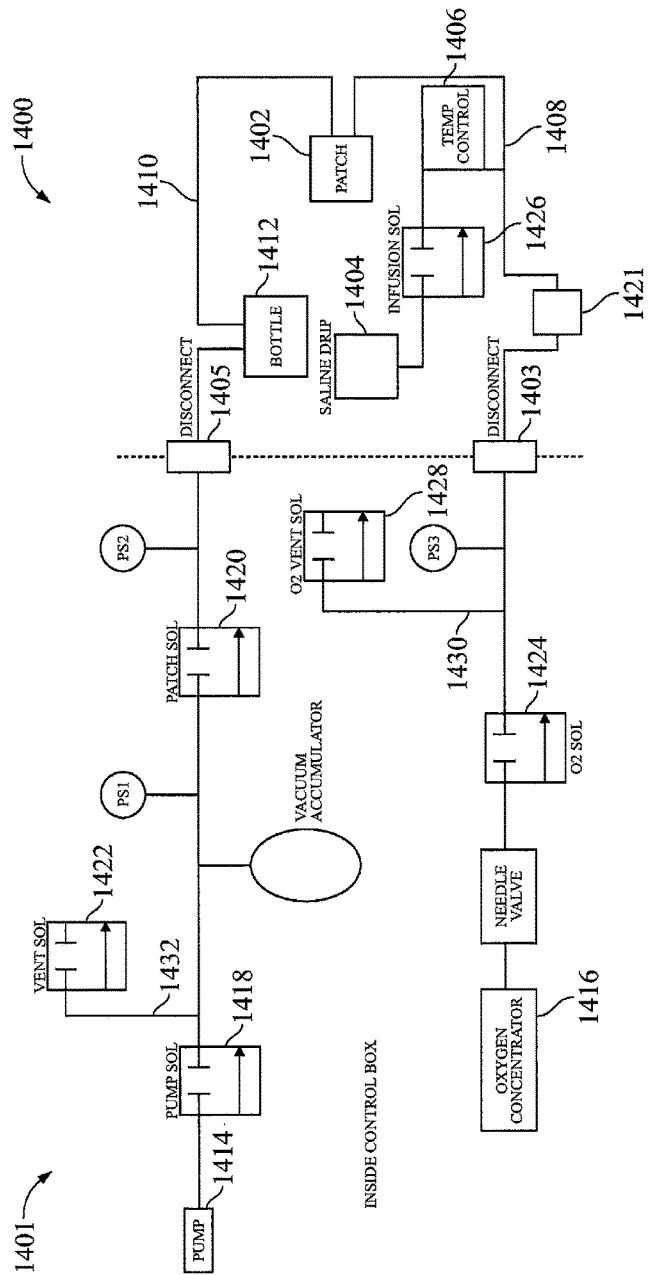
FIG. 14 is a schematic diagram of a wound-infusion system according to an exemplary embodiment.

FIG. 14 is a schematic diagram of a wound-infusion system according to an exemplary embodiment. The wound-infusion system 1400 includes a controller 1401 having a first disconnect 1403 and a second disconnect 1405. The first disconnect 1403 is fluidly coupled to an oxygen concentrator 1416 and the second disconnect 1405 is fluidly coupled to a pump 1414. A patch 1402 includes an infusion tube 1408 and a negative-pressure tube 1410. The infusion tube 1408 is fluidly coupled to the first disconnect 1403 and the negative-pressure tube 1410 is fluidly coupled to the second disconnect 1405. Thus, in operation, negative-pressure pressure, generated by the pump 1414, is applied to the patch 1402 via the second disconnect 1405 and the negative-pressure tube 1410. Similarly, oxygen, supplied by the oxygen concentrator 1416, is applied to the patch 1402 via the first disconnect 1403 and the infusion tube 1408.

Still referring to FIG. 14, a reservoir 1404 is provided with the patch 1402. In a typical embodiment, the reservoir contains a therapeutic agent such as, for example, saline. The reservoir 1404 is fluidly coupled to the infusion tube 1408 via an infusion solenoid 1426 and a temperature control 1406. In a typical embodiment, the infusion solenoid 1426, when open, fluidly couples the reservoir 1404 to the patch 1402 via the infusion tube 1408. Thus, oxygen, supplied by the oxygen concentrator 1416, pushes the therapeutic agent through the infusion tube 1408 to the patch 1402. In a typical embodiment, oxygen supplied by the oxygen concentrator 1416 passes through humidifier 1421. The humidifier 1421 facilitates delivery of oxygen that is humidified above ambient humidity to the wound site. In a typical embodiment, the oxygen delivery is at a partial pressure of approximately 22 mmHg. When closed, the infusion solenoid 1426 isolates the reservoir 1404 from the infusion tube 1408 and the patch 1402. In a various embodiment, the temperature control 1406 may regulate a temperature of the therapeutic agent thereby facilitating application of thermal therapy to a wound area (not shown) via the patch 1402. For example, in various embodiments, the temperature control 1406 may raise the temperature of the therapeutic agent to a level above a body temperature of a patient. An exudate bottle 1412 is fluidly coupled to the negative-pressure tube 1410. During operation, the exudate bottle 1412 collects fluids and materials removed through the patch 1402 by operation of negative-pressure pressure supplied by the pump 1414. Thus, the pump 1414 remains sterile during operation.

Still referring to FIG. 14, an oxygen solenoid 1424 is disposed within the controller 1401 and is fluidly coupled to the oxygen concentrator 1416 and the first disconnect 1403. When open, the oxygen solenoid 1424 fluidly couples the oxygen concentrator 1416 to the first disconnect 1403. When closed, the oxygen solenoid 1424 isolates the oxygen concentrator 1416. An oxygen vent 1430 is fluidly coupled to oxygen concentrator 1416, the oxygen solenoid 1424, the first disconnect 1403 and an exterior environment. During operation, the oxygen vent 1430 allows oxygen supplied by the oxygen concentrator 1416 to be vented to the exterior environment. An oxygen-vent solenoid 1428 is fluidly coupled to the oxygen vent 1430. When open, the oxygen-vent solenoid 1428 allows oxygen supplied by the oxygen concentrator 1416 to be vented to the exterior environment. When closed, the oxygen-vent solenoid 1428 prevents oxygen supplied by the oxygen concentrator 1416 from being vented to the exterior environment. In a typical embodiment, the oxygen supplied by the concentrator is in the range of approximately 75% to approximately 100% oxygen.

Still referring to FIG. 14, a pump solenoid 1418 is disposed within the controller 1401 and fluidly coupled to the pump 1414 and the second disconnect 1405. When open, the pump solenoid 1418 fluidly couples the pump 1414 to the second disconnect 1405. When closed, the pump solenoid 1418 isolates the pump 1414. A negative-pressure vent 1432 is fluidly coupled to pump 1414, the pump solenoid 1418, the second disconnect 1405 and an exterior environment. During operation, the negative-pressure vent 1432 allows pressure generated by the pump 1414 to be vented to the exterior environment. A negative-pressure-vent solenoid 1422 is fluidly coupled to the negative-pressure vent 1432. When open, the negative-pressure-vent solenoid 1422 allows pressure generated by the pump 1414 to be vented to the exterior environment. When closed, the negative-pressure-vent solenoid 1422 prevents pressure generated by the pump 1414 from being vented to the exterior environment. A patch solenoid 1420 is fluidly coupled to the pump 1414 between the negative-pressure vent 1432 and the second disconnect 1405. When open, the patch solenoid 1420 fluidly couples the second disconnect 1405 to the pump 1414. When closed, the patch solenoid 1420 isolates the second disconnect 1405 and the patch 1402. The patch solenoid 1420, when closed facilitates testing of the patch 1402 to ensure a proper seal with the wound area (not shown).

Figure 15:
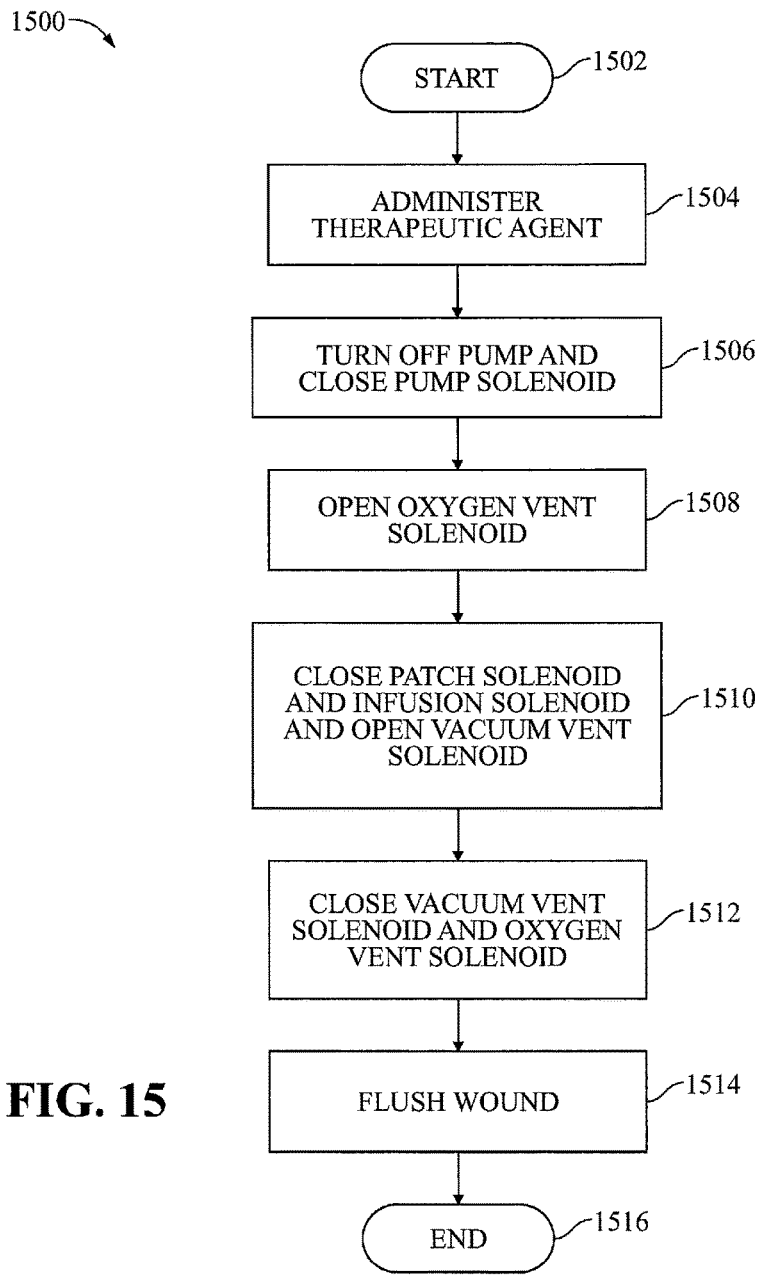
FIG. 15 is a flow diagram of a process for administering infusion therapy in conjunction with negative-pressure therapy and oxygenation therapy according to an exemplary embodiment.

FIG. 15 is a flow diagram of a process for administering infusion therapy in conjunction with negative-pressure therapy and oxygenation therapy according to an exemplary embodiment. A process 1500 begins at step 1502. At step 1504, a therapeutic agent such as, for example, saline, any wound-treating drugs, antibiotics, or any combination thereof is administered to a wound area via the patch 1402. Negative-pressure pressure is also administered to the wound area via the patch 1402. In a typical embodiment, the negative-pressure pressure is in the range of approximately 0 mmHg to approximately 150 mmHg During step 1504, the temperature control 1406 regulates the temperature of the therapeutic agent to achieve a therapeutically-beneficial temperature. In a typical embodiment, the therapeutically-beneficial temperature is in the range of ambient temperature to approximately 105° F. In a typical embodiment, step 1504 has a duration of approximately 10 seconds. At step 1506, the pump 1414 is turned off and the pump solenoid 1418 is closed. The therapeutic agent continues to be administered to the wound area via the patch 1402. In a typical embodiment, step 1506 has a duration of approximately 10 seconds.

At step 1508, the oxygen-vent solenoid 1428 is opened allowing oxygen supplied by the oxygen concentrator 1416 to be vented to the exterior environment. In a typical embodiment, step 1508 has a duration of approximately 5 seconds. At step 1510, the patch solenoid 1420 and the infusion solenoid 1428 are closed while the negative-pressure vent solenoid 1422 and the oxygen vent solenoid 1424 are opened. In a typical embodiment, step 1510 has a duration of approximately 20 seconds. At step 1512, the negative-pressure vent solenoid 1422 and the oxygen vent solenoid 1424 are closed. In a typical embodiment, step 1512 has a duration of approximately 15 minutes to approximately 16 minutes. At step 1514, the pump solenoid 1418, the patch solenoid 1420, the oxygen vent solenoid 1428 are opened thereby allowing the wound area to be flushed. In a typical embodiment, step 1514 has a duration of approximately 30 seconds. The process ends at step 1516.

Figure 16:
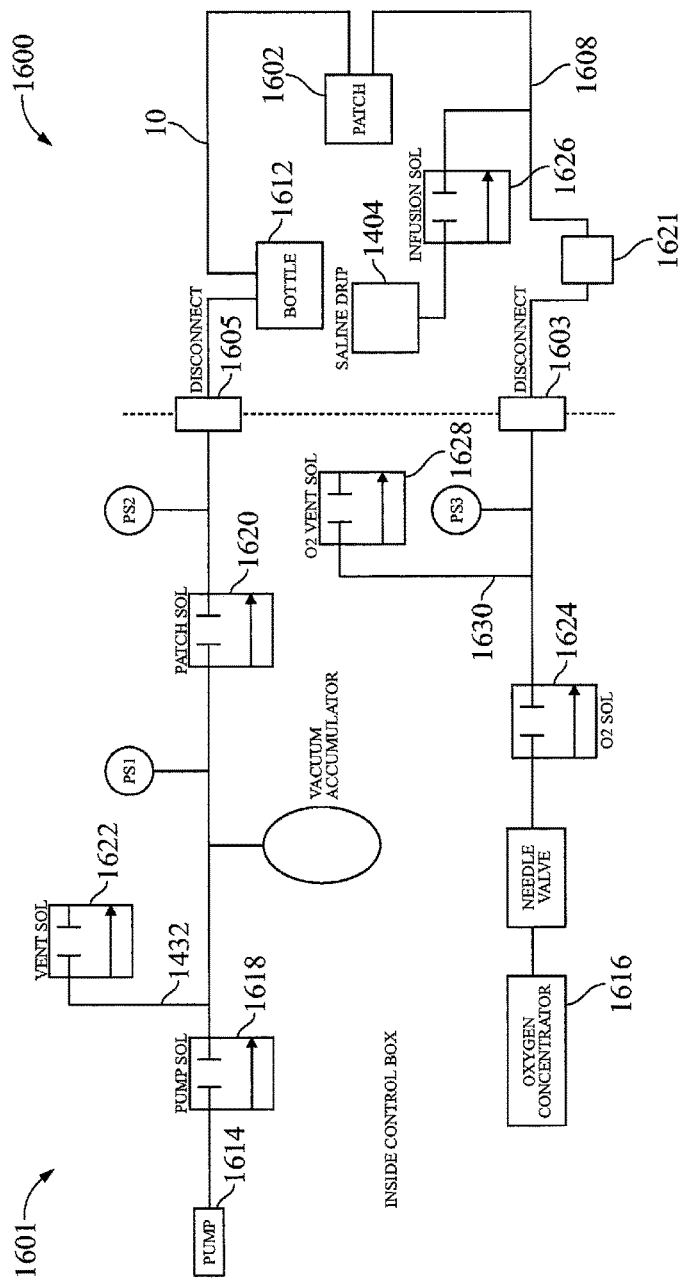
FIG. 16 is a schematic diagram of a wound-care system according to an exemplary embodiment.

FIG. 16 is a schematic diagram of a wound-care system according to an exemplary embodiment. The wound-care system 1600 includes a controller 1601 having a first disconnect 1603 and a second disconnect 1605. The first disconnect 1603 is fluidly coupled to an oxygen concentrator 1616 and the second disconnect 1605 is fluidly coupled to a pump 1614. A patch 1602 includes an infusion tube 1608 and a negative-pressure tube 1610. The infusion tube 1608 is fluidly coupled to the first disconnect 1603 and the negative-pressure tube 1610 is fluidly coupled to the second disconnect 1605. Thus, in operation, negative-pressure pressure, generated by the pump 1614, is applied to the patch 1602 via the second disconnect 1605 and the negative-pressure tube 1610. Similarly, oxygen, supplied by the oxygen concentrator 1616, is applied to the patch 1602 via the first disconnect 1603 and the infusion tube 1608.

Still referring to FIG. 16, oxygen supplied by the oxygen concentrator 1616 passes through humidifier 1621. The humidifier 1621 facilitates delivery of oxygen that is humidified above ambient humidity to the wound site. In a typical embodiment, the oxygen delivery is at a partial pressure of approximately 22 mmHg. An exudate bottle 1612 is fluidly coupled to the negative-pressure tube 1610. During operation, the exudate bottle 1612 collects fluids and materials removed through the patch 1602 by operation of negative-pressure pressure supplied by the pump 1614. Thus, the pump 1614 remains sterile during operation.

Still referring to FIG. 16, an oxygen solenoid 1624 is disposed within the controller 1601 and is fluidly coupled to the oxygen concentrator 1616 and the first disconnect 1603. When open, the oxygen solenoid 1624 fluidly couples the oxygen concentrator 1616 to the first disconnect 1603. When closed, the oxygen solenoid 1624 isolates the oxygen concentrator 1616. An oxygen vent 1630 is fluidly coupled to oxygen concentrator 1616, the oxygen solenoid 1624, the first disconnect 1603 and an exterior environment. During operation, the oxygen vent 1630 allows oxygen supplied by the oxygen concentrator 1616 to be vented to the exterior environment. An oxygen-vent solenoid 1628 is fluidly coupled to the oxygen vent 1630. When open, the oxygen-vent solenoid 1628 allows oxygen supplied by the oxygen concentrator 1616 to be vented to the exterior environment. When closed, the oxygen-vent solenoid 1628 prevents oxygen supplied by the oxygen concentrator 1616 from being vented to the exterior environment. In a typical embodiment, the oxygen supplied by the concentrator is in the range of approximately 75% to approximately 100% oxygen.

Still referring to FIG. 16, a pump solenoid 1618 is disposed within the controller 1601 and fluidly coupled to the pump 1614 and the second disconnect 1605. When open, the pump solenoid 1618 fluidly couples the pump 1614 to the second disconnect 1605. When closed, the pump solenoid 1618 isolates the pump 1614. A negative-pressure vent 1632 is fluidly coupled to pump 1614, the pump solenoid 1618, the second disconnect 1605 and an exterior environment. During operation, the negative-pressure vent 1632 allows pressure generated by the pump 1614 to be vented to the exterior environment. A negative-pressure-vent solenoid 1622 is fluidly coupled to the negative-pressure vent 1632. When open, the negative-pressure-vent solenoid 1622 allows pressure generated by the pump 1614 to be vented to the exterior environment. When closed, the negative-pressure-vent solenoid 1622 prevents pressure generated by the pump 1614 from being vented to the exterior environment. A patch solenoid 1620 is fluidly coupled to the pump 1614 between the negative-pressure vent 1632 and the second disconnect 1605. When open, the patch solenoid 1620 fluidly couples the second disconnect 1605 to the pump 1614. When closed, the patch solenoid 1620 isolates the second disconnect 1605 and the patch 1602. The patch solenoid 1620, when closed facilitates testing of the patch 1602 to ensure a proper seal with the wound area (not shown).

Figure 17:
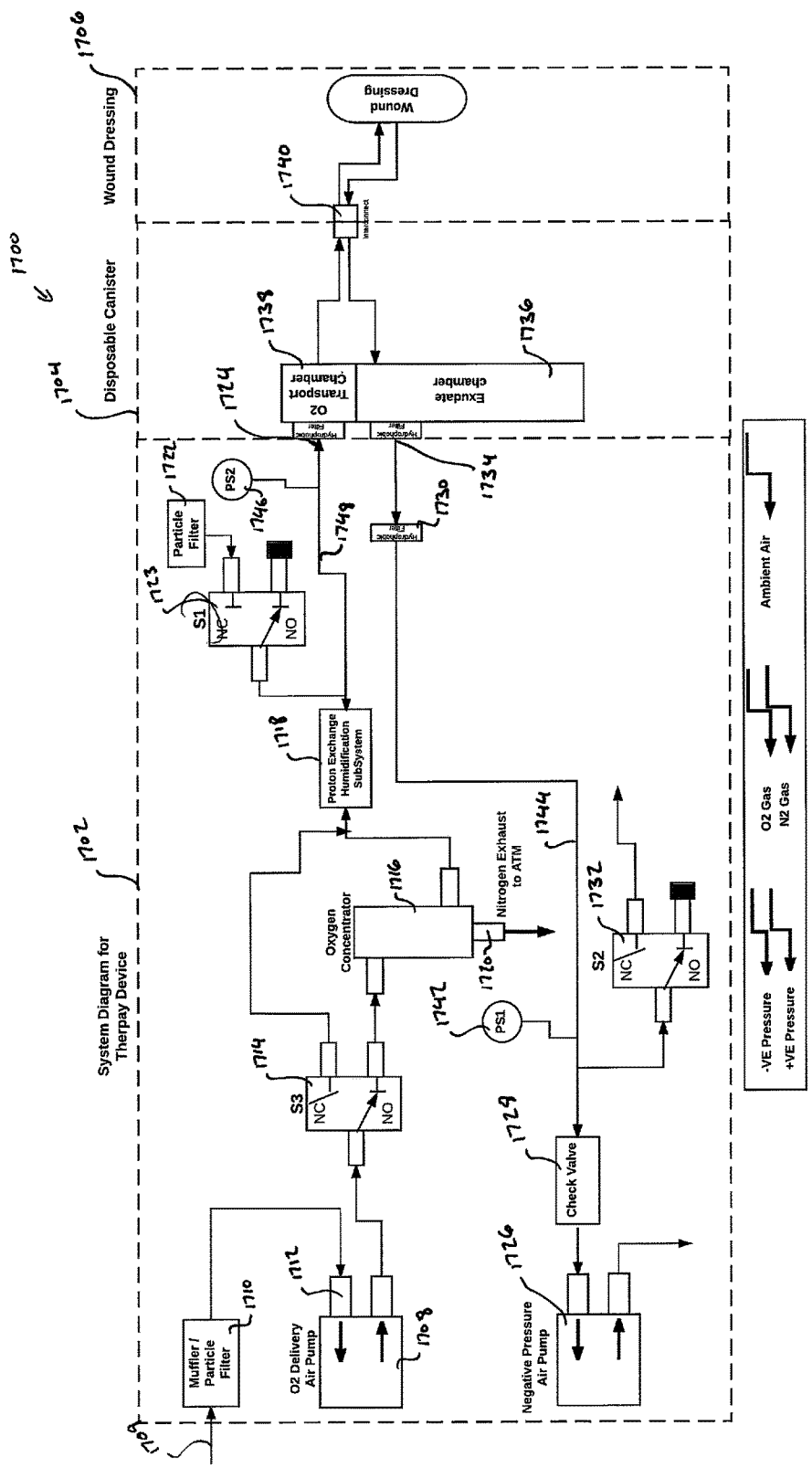
FIG. 17 is a schematic diagram of a wound-care system according to an exemplary embodiment.

Referring now to FIG. 17, there is shown a schematic diagram of a wound-care system 1700. In a typical embodiment, the wound-care system 1700 is configured to deliver at least one of a first treatment modality, including oxygen-rich fluid therapy, and a second treatment modality, including negative-pressure therapy to wound. The wound-care system 1700 includes a therapy device 1702, a disposable canister 1704, and a wound dressing 1706. The therapy device 1702 includes a first pump 1708 that facilitates delivery of, for example, an oxygen-rich fluid, to a wound site. A particle filter 1710 is fluidly coupled to an inlet 1712 of the first pump 1708. In a typical embodiment, the first pump 1708 draws fluids 1709 such as, for example, ambient air through the inlet 1712 and the particle filter 1710; however, in other embodiments, the first pump 1708 draws fluids 1709 such as, for example, gaseous oxygen from, for example, a hospital central oxygen source or an oxygen cylinder. The first pump 1708 is fluidly coupled to a first valve 1714. The first valve 1714 may typically be a solenoid valve and, in a first position, directs a flow of fluid from the first pump to an oxygen concentrator 1716. When in a second position, the first valve 1714 directs the flow of fluid from the first pump 1708 to bypass the oxygen concentrator 1716 and proceed directly to a humidification system 1718. In a typical embodiment, the oxygen concentrator 1716 is, for example, a pressure-swing adsorption device, an electrochemical device, or any other appropriate device. In a typical embodiment, a pressure-swing adsorption device includes at least one adsorptive material such as, for example, zeolite, activated carbon, molecular sieves, or any other adsorptive material as dictated by design requirements. The adsorptive material adsorbs, for example, nitrogen from ambient air. By removing nitrogen from the ambient air, the oxygen concentrator 1716 creates a fluid mixture having a higher concentration of oxygen than ambient air. By way of example, the fluid mixture discharged from the oxygen concentrator 1716 has an oxygen concentration above ambient oxygen levels; however, in other embodiments, different concentrations can be utilized as dictated by design requirements. For purposes of discussion, the fluid mixture discharged from the oxygen concentrator 1716 is referred to herein as "the oxygen-rich fluid;" however, one skilled in the art will recognize that trace amounts of other fluids may be present in the oxygen-rich fluid. The oxygen concentrator

1716 includes an exhaust 1720. During operation, accumulated nitrogen is released to an environment via the exhaust 1720.

Still referring to FIG. 17, the oxygen-rich fluid is discharged from the oxygen concentrator 1716 and flows to the humidification system 1718. During operation, the oxygen-rich fluid discharged from the oxygen concentrator 1716 is at a lower relative humidity than ambient air. In a typical embodiment, the humidification system 1718 includes, for example, a plurality proton-exchange membrane tubes. The oxygen-rich fluid discharged from the oxygen concentrator 1716 is passed within the proton-exchange membrane tubes. The humidification system 1718 draws in ambient air, which is at a higher relative humidity than the oxygen-rich fluid discharged from the oxygen concentrator 1716, through a particle filter 1722 and a second valve 1723. The ambient air flows around an outside of the proton-exchange membrane tubes thereby creating a humidity gradient between the low-humidity the oxygen-rich fluid and the higher-humidity ambient air. Moisture is drawn from the ambient air across the proton-exchange membrane tube and into the oxygen-rich fluid thereby increasing a relative humidity of the oxygen-rich fluid. In other embodiments, the humidification system 1718 may include the channel 1738 containing sterile water and disposed in the disposable canister 1704. The oxygen-rich fluid is passed through the sterile water in the channel 1738 and humidified by the sterile water. From the humidification system 1718, the oxygen-rich fluid flows to a coupling device 1724. In a typical embodiment, the coupling device 1724 provides a fluid link to the disposable canister 1704.

Still referring to FIG. 17, the therapy device 1702 includes a second pump 1726 that draws fluid from the wound dressing 1706. In a typical embodiment, operation of the second pump 1726 may be a negative-pressure pump that causes an area under the wound dressing 1706 being maintained at a pressure below ambient pressure. However, in other embodiments, the second pump 1726 could be utilized to increase a pressure of the area under the wound dressing 1706 to a level above ambient pressure. In still other embodiments, the second pump 1726 could be utilized to maintain the area under the wound dressing 1706 at a pressure approximately equal to ambient pressure. The second pump 1726 draws fluids through a check valve 1728 and a filter 1730. In a typical embodiment, the filter 1730 is a backup filter that prevents exudate from the wound from entering the second pump 1726. A third valve 1732 provides a vent to an exterior environment. In a typical embodiment, the third valve 1732 is a solenoid valve. The second pump 1726 is fluidly coupled, via the filter 1730 and the check valve 1728 to a coupling device 1734. In a typical embodiment, the coupling device 1734 provides a fluid link to the disposable canister 1704.

Still referring to FIG. 17, the disposable container 1704 includes an exudate chamber 1736 and a channel 1738. In a typical embodiment, fluid debris, tissue, and other materials that are removed from the wound by the second pump 1726 are collected in the exudate chamber 1736. In a typical embodiment, the channel 1738 provides a buffer chamber for the oxygen-rich fluid that is applied to the wound dressing 1706 and thereby accommodates slight variations in pressure of the oxygen-rich fluid. The disposable canister 1704 may be selectively removable from the therapy device 1702. In a typical embodiment, the disposable canister 1704 is removed, for example, when the exudate chamber 1736 is full. The disposable canister 1704 may then be disposed of and replaced. The exudate chamber 1736 and the channel 1738 are fluidly coupled to a coupling device 1740. In a typical embodiment, the coupling device 1740 provides a fluid link to the wound dressing 1706. The wound dressing 1706 is placed over a wound and conducts at least one of the oxygen-rich fluid and negative pressure to the wound. In a typical embodiment, the first pump 1708 and the second pump 1726 are operated independently of each other. Thus, the first pump 1708 and the second pump 1726 may be operated simultaneously or sequentially depending on a nature of the wound and treatment requirements. That is, in various embodiments, the oxygen-rich fluid and negative pressure may be applied to the wound in a simultaneous or sequential fashion.

Still referring to FIG. 17, a first pressure sensor 1742 is disposed proximate the second pump 1726 and exposed to pressure in a negative-pressure tube 1744. Thus, the first pressure sensor 1742 measures pressure in the negative-pressure tube 1744. A second pressure sensor 1746 is disposed proximate a fluid tube 1748. In other embodiments, however, the second pressure sensor 1746 is disposed on an outer surface of the wound dressing 1706. During operation, the wound-care system 1700 may be operated to provide negative-pressure treatment simultaneously with oxygen-rich fluid treatment. In such a situation, the first pump 1708 and the second pump 1726 are activated simultaneously. In other embodiments, the wound-care system 1700 provides one of negative-pressure treatment and oxygen-rich fluid treatment sequentially. In such an arrangement the first pump 1708 and the second pump 1726 are operated sequentially. The first pump 1708 and the second pump 1726 are typically peristaltic pumps. Thus, during operation, the first pump 1708 may cause slight pressure variations in the fluid tube 1748. In an effort to prevent pressure artifacts from the first pump 1706 from impacting the measured wound pressure, during periods where the first pump 1708 is operated alone, thereby providing oxygen-rich fluid therapy only to the wound, a pressure at the wound is monitored using the first pressure sensor 1742 due to the possibility of pressure artifacts at the second pressure sensor 1746. Alternatively, when the second pump 1726 is operated alone, thereby providing negative-pressure therapy only to the wound, a pressure at the wound is monitored using the second pressure sensor 1746 due to pressure variations being present in the negative-pressure tube 1744 from the peristaltic operation of the second pump 1726.

Figure 18:
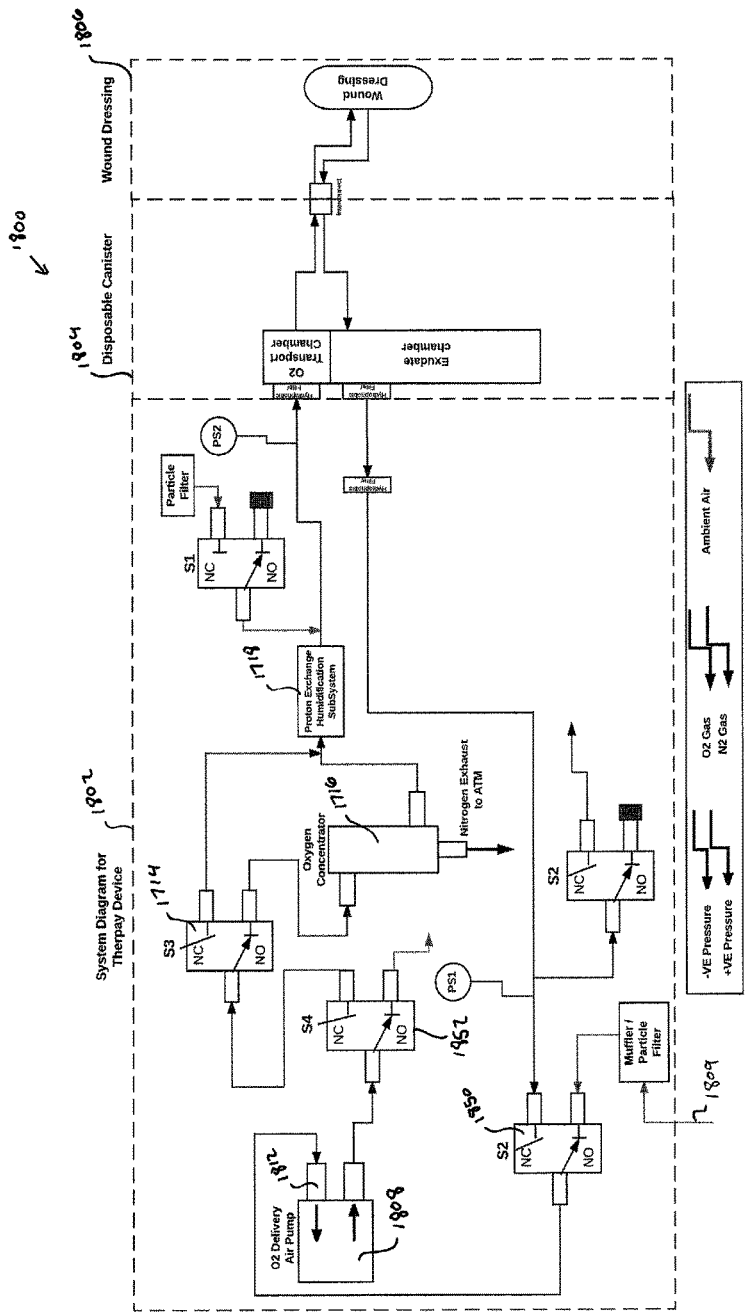
FIG. 18 is a schematic diagram of a wound-care system utilizing a single pump according to an exemplary embodiment.

FIG. 18 is a schematic diagram of a wound-care system 1800 utilizing a single pump. The wound-care system 1800 includes a therapy device 1802, the disposable container 1704, and the wound dressing 1706. The therapy device 1802 includes a pump 1808. The pump 1808 draws fluid through an inlet 1812. The inlet 1812 is fluidly coupled to a fourth valve 1850. In a typical embodiment, the fourth valve 1850 is a solenoid valve that, in a first position allows fluids 1809 such as, for example, ambient air to be drawn into the inlet 1812. In a second position, the fourth valve facilitates drawing of fluid from the wound dressing 1706 into the inlet 1812. Fluid discharged from the pump 1808 enters a fifth valve 1852. The fifth valve 1852 is a solenoid valve that, in a first position transmits fluid discharged from the pump 1808 to the first valve 1714. In a second position, the fifth valve 1852 vents fluid discharged from the pump 1808 to the atmosphere. Fluid discharged from the first valve passes through the oxygen concentrator 1716, the humidification system 1718, and into the wound dressing 1706 as described above with respect to FIG. 17. In this manner, the wound-care system 1800 facilitates delivery of oxygen-rich fluid and negative pressure to the wound dressing 1706 with the use of a single pump.

Figure 19A:
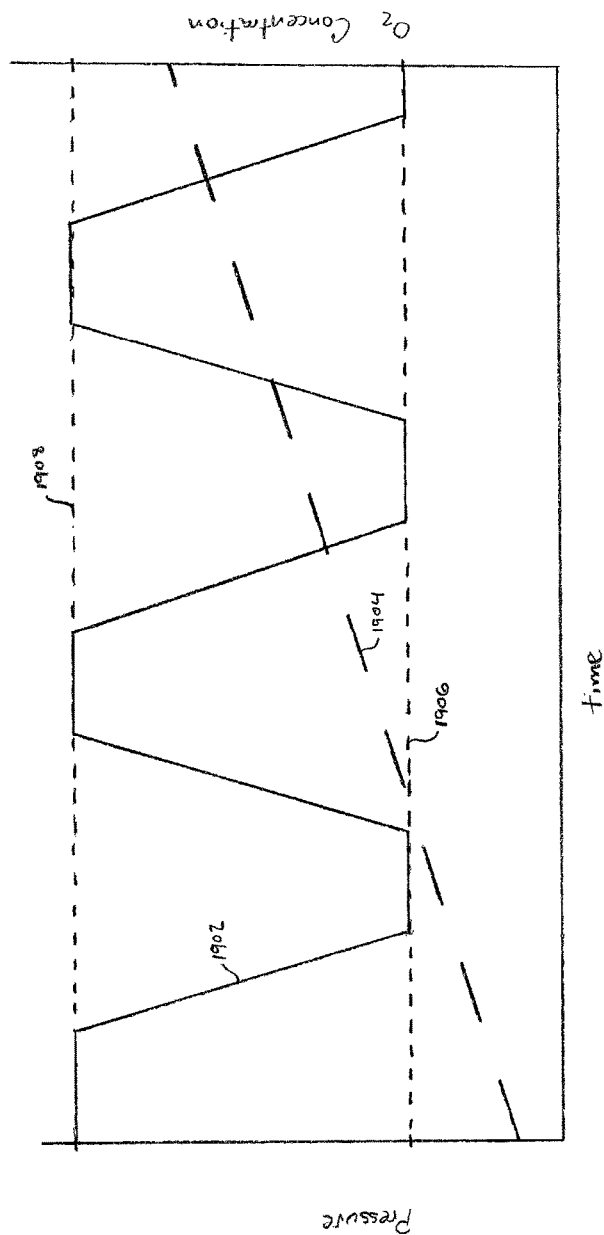
FIG. 19A is a graph of pressure versus time illustrating a first embodiment of simultaneous application of negative pressure and oxygen-rich fluid.

FIG. 19A is a graph of pressure versus time illustrating a first embodiment of simultaneous application of negative pressure and oxygen-rich fluid. FIG. 19A is a graphical illustration of a first treatment methodology in which variations in pressure are illustrated by the line 1902 and oxygen concentration is illustrated by the line 1904. During operation, the wound dressing 1706 is evacuated to a high negative-pressure state (illustrated by line 1906). Simultaneously, oxygen-rich fluid is supplied to the wound dressing 1706. After a first pre-determined period of time, the pressure under the wound dressing 1706 is raised to the low-negative-pressure state (illustrated by line 1908) for a second pre-determined period of time. After the second pre-determined period of time, the pressure under the wound dressing 1706 is again lowered to the high-negative-pressure state. This pattern of alternating between the high-negative-pressure state and the low-negative-pressure state is repeated for the duration of the treatment. Simultaneous to the application of negative pressure, oxygen-rich fluid is applied to the wound dressing 1706. With each successive pressure cycle, the concentration of oxygen under the wound dressing 1706 increases to a point where the oxygen concentration under the wound dressing 1706 is approximately equal to the oxygen concentration of the oxygen-rich fluid discharged from the oxygen concentrator 1716. Although FIG. 19A has been described herein as being used in conjunction with the wound-care system 1700, one skilled in the art will recognize that the wound-care device 1800 could also be utilized to deliver the therapeutic modalities illustrated in FIG. 19A.

Figure 19B:
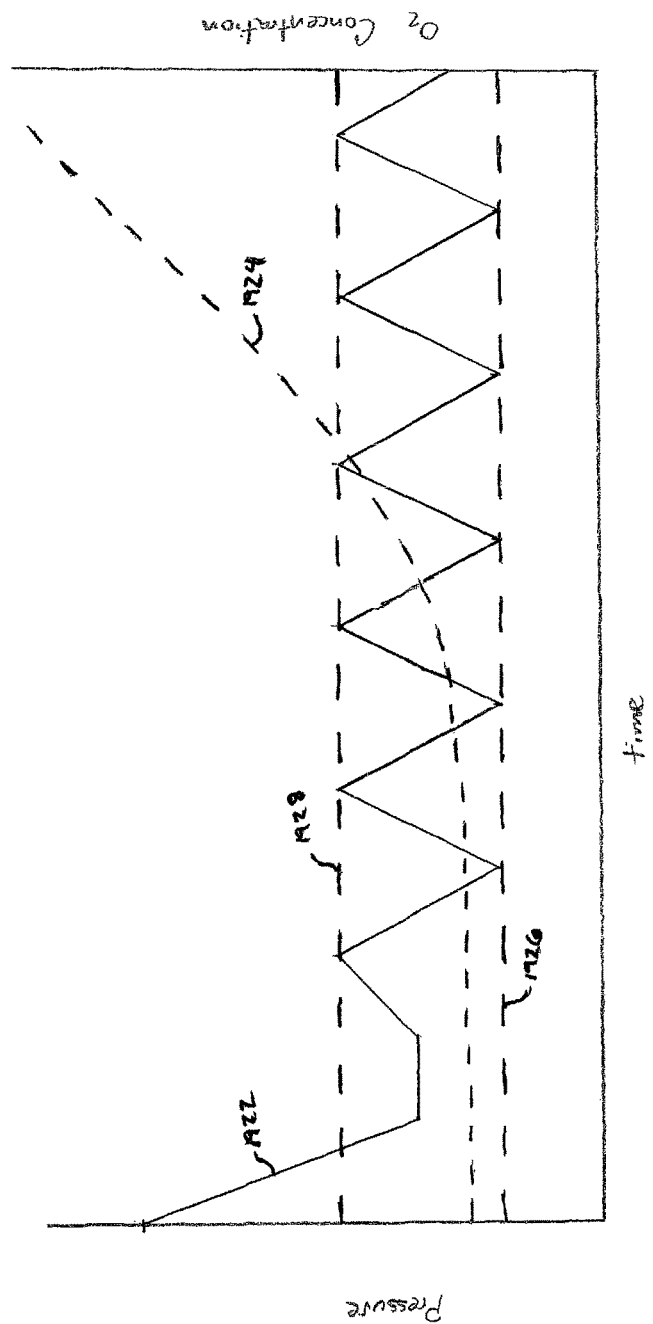
FIG. 19B is a graph of pressure versus time illustrating a second embodiment of simultaneous application of negative pressure and oxygen-rich fluid.

FIG. 19B is a graph of pressure versus time illustrating a second embodiment of simultaneous application of negative pressure and oxygen-rich fluid. FIG. 19B is a graphical illustration of a second treatment methodology in which variations in pressure are illustrated by the line 1922 and oxygen concentration is illustrated by the line 1924. During operation, the wound dressing 1706 is evacuated to the high-negative-pressure state. After a first predetermined period of time, the pressure under the wound dressing is alternatingly raised and lowered within specified limits (illustrated by lines 1926 and 1928) such as, for example, approximately 5-10 mmHg. The raising and lowering of pressure under the wound dressing 1706 causes the pressure 1922 to assume the saw-tooth like shape illustrated in FIG. 18B. Simultaneous to application of negative pressure, oxygen-rich fluid is applied to the wound dressing 1706. The alternating raising and lowering of the pressure under the wound dressing 1706 causes the oxygen concentration under the wound dressing 1706 to gradually rise. In a typical embodiment, in the embodiment shown in FIG. 19B, the oxygen concentration under the wound dressing 1706 rises at a slower rate than the oxygen concentration illustrated in FIG. 19A. In a typical embodiment, the oxygen concentration under the wound dressing 1706 continues to rise until the oxygen concentration under the wound dressing 1706 is approximately equal to the oxygen concentration of the oxygen-rich fluid discharged from the oxygen concentrator 1716. Although FIG. 19B has been described herein as being used in conjunction with the wound-care system 1700, one skilled in the art will recognize that the wound-care device 1800 could also be utilized to deliver the therapeutic modalities illustrated in FIG. 19B.

Figure 19C:
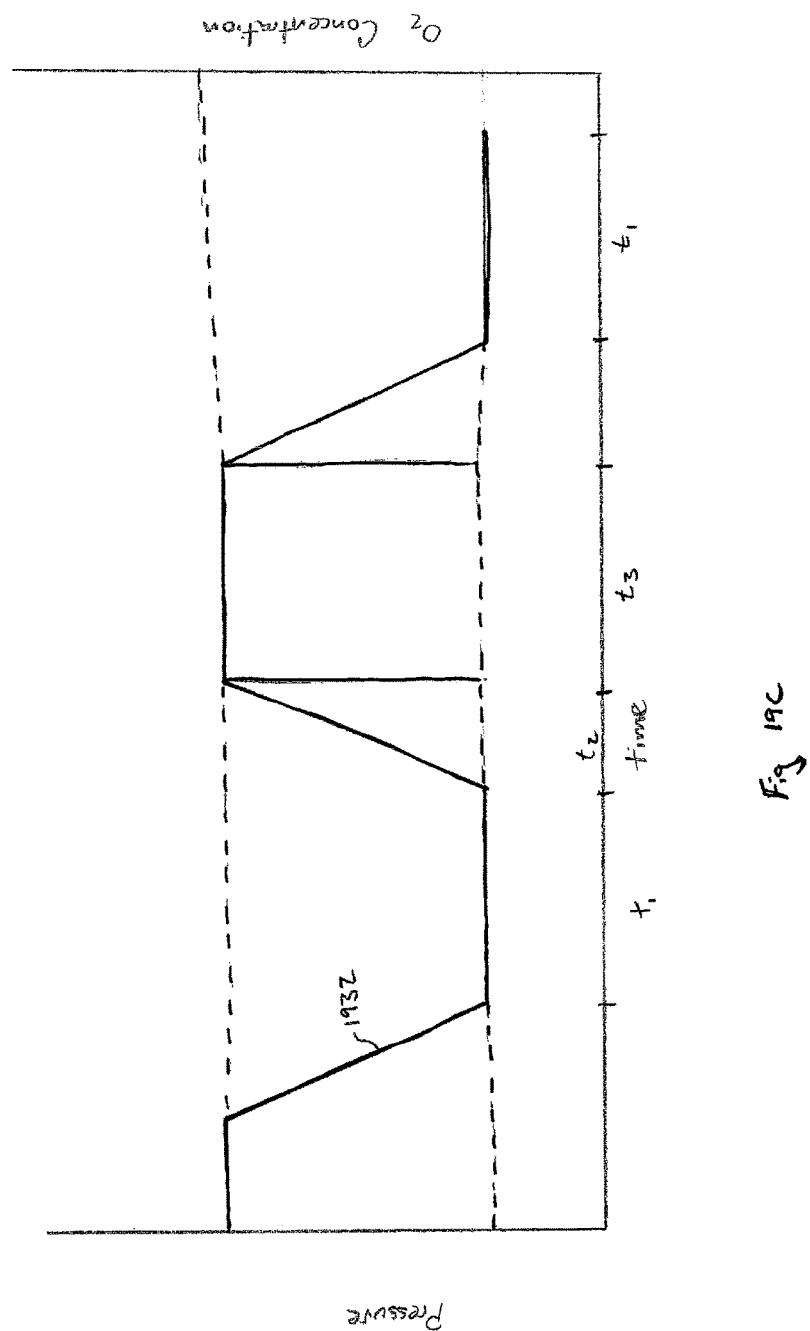
FIG. 19C is a graph of pressure versus time illustrating sequential application of negative pressure and oxygen-rich fluid.

FIG. 19C is a graph of pressure versus time illustrating sequential application of negative pressure and oxygen-rich fluid. FIG. 19C is a graphical illustration of a third treatment methodology in which variations in pressure are illustrated by the line 1932. During operation, the wound dressing 1706 is evacuated to the high-negative-pressure state for a first pre-determined period of time (t1). After the first predetermined period of time (t1), negative pressure is no longer applied to the wound dressing 1706 and oxygen-rich fluid is applied to the wound dressing for a second pre-determined period of time (t2). Application of the oxygen-rich fluid to the wound dressing 1706 raises a pressure under the wound dressing 1706. The oxygen rich fluid is held under the wound dressing 1706 for a third pre-determined period of time (t3). After the third pre-determined period of time (t3), negative pressure is applied to the wound dressing 1706 and the pressure is lowered to the high-negative-pressure state. The wound dressing is held at the high-negative-pressure state for the first pre-determined period of time (t1). This pattern repeats for the duration of the treatment. Although FIG. 19C has been described herein as being used in conjunction with the wound-care system 1700, one skilled in the art will recognize that the wound-care device 1800 could also be utilized to deliver the therapeutic modalities illustrated in FIG. 19C.

Figure 20:
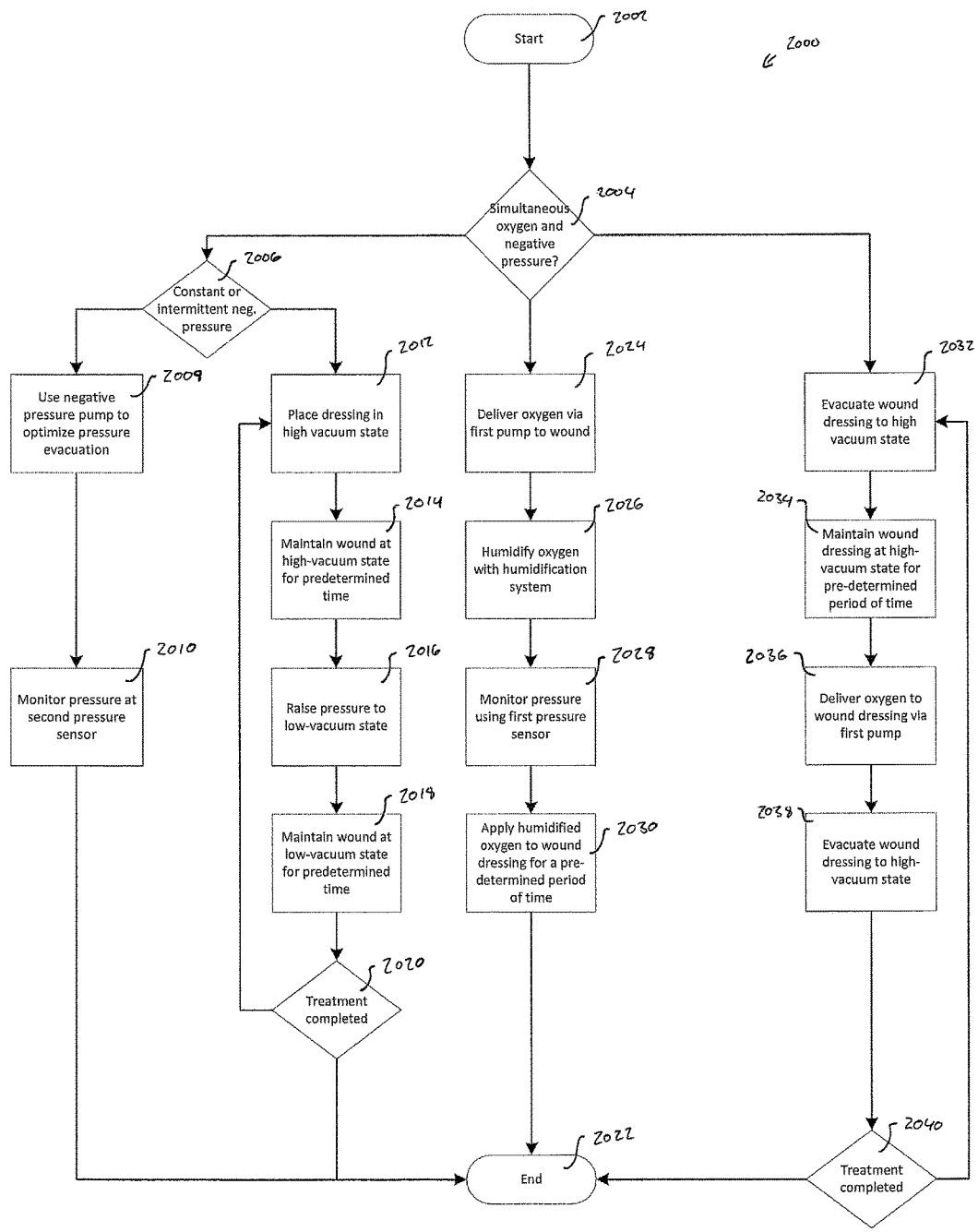
FIG. 20 is a flow diagram of a process for treating a wound according to an exemplary embodiment.

Referring now to FIG. 20, there is shown a flow diagram of a process 2000 for treating a wound. The process 2000 begins at step 2002. At step 2004, it is determined if the wound-care system 1700 will provide negative-pressure therapy, oxygen-rich fluid therapy, or simultaneous negative-pressure and oxygen-rich fluid therapy. Responsive to a determination that the wound-care system 1700 will provide negative-pressure therapy, the process 2000 proceeds to step 2006. At step 2006, it is determined if the wound-care system 1700 will provide constant or intermittent negative pressure. Responsive to a determination that constant negative-pressure will be provided, the process 2000 proceeds to step 2008. At step 2008, the second pump 1726 is utilized to optimize pressure evacuation from an area under the wound dressing 1706. At step 2010, a pressure under the wound dressing 1706 is monitored utilizing the second pressure sensor 1746. The negative pressure is maintained under the wound dressing 1706 for the duration of treatment. The process 2000 ends at step 2022.

Still referring to FIG. 20, if it is determined at step 2006 that intermittent negative pressure should be provided, the process 2000 proceeds to step 2012. At step 2012, the second pump 1726 is utilized to evacuate an area under the wound dressing 1706 to a high-negative-pressure state. In a typical embodiment, the high-negative-pressure state exposes an area under the wound dressing 1706 to a pressure of, for example, just below zero mmHg to approximately −300 mmHg. At step 2014, the area under the wound dressing 1706 is maintained at the high-negative-pressure state for a pre-determined period of time. At step 2016, after the pre-determined period of time has elapsed, the pressure under the wound dressing 1706 is raised to a low-negative-pressure state. In a typical embodiment, the low-negative-pressure state is at a pressure that is higher than the high-negative-pressure state. In a typical embodiment, the pressure under the wound dressing 1706 is raised by opening the third valve 1732. Opening the third valve 1732 allows ambient air to enter the wound-care system 1700 and thereby raises the pressure under the wound dressing 1706. At step 2018, the pressure under the wound dressing 1706 is maintained at the low-negative-pressure state for a second pre-determined period of time. After the second pre-determined period of time has elapsed, at step 2020 it is determined if treatment is completed. Responsive to a determination in step 2020 that treatment is not completed, the process 2000 repeats to step 2012 and the second pump 1726 is utilized to evacuate the area under the wound dressing 1706 to the high-negative-pressure state. Responsive to a determination at step 2020 that treatment is completed, the process 2000 ends at step 2022.

Still referring to FIG. 20, responsive to a determination at step 2004 only oxygen-rich fluid therapy should be provided, the process 2000 proceeds to step 2024. At step 2024, the first pump 1708 is utilized to supply the oxygen-rich fluid to the wound dressing 1706. At step 2026, the oxygen-rich fluid supplied by the first pump 1708 is humidified via the humidification system 1718. At step 2028, a pressure under the wound-dressing 1706 is monitored via the first pressure sensor 1742. In a typical embodiment, introduction of the oxygen-rich fluid to the area under the wound dressing 1706 increases a pressure under a wound dressing 1706 to near atmospheric pressure. At step 2030, the oxygen-rich fluid is supplied to the wound dressing 1706 for a pre-determined period of time. After the pre-determined period of time has elapsed, the process 2000 ends at step 2022.

Still referring to FIG. 20, if it is determined at step 2004 that simultaneous application of oxygen-rich fluid therapy and negative pressure should be provided, the process 2000 proceeds to step 2032. At step 2032, the second pump 1726 is utilized to evacuate the area under the wound dressing 1706 to the high-negative-pressure state. At step 2034, the area under the wound dressing 1706 is maintained at the high-negative-pressure state for a pre-determined period of time. At step 2036, the first pump 1708 is utilized to deliver the oxygen-rich fluid to the wound dressing 1706. In a typical embodiment, delivery of the oxygen-rich fluid to the wound dressing 1706 raises a pressure under the wound dressing 1706 for a pre-determined time period. In various embodiments, the delivery of the oxygen-rich fluid under the wound dressing 1706 raises a pressure under the wound dressing to approximately the low-negative-pressure state. In other embodiments, the delivery of the oxygen-rich fluid raises the pressure under the wound dressing 1706 to a neutral-pressure state. That is, the pressure under the wound dressing is approximately equal to ambient atmospheric pressure. In still other embodiments, the delivery of the oxygen-rich fluid raises the pressure under the wound dressing to a pressure that is slightly above atmospheric pressure but less than venous backflow pressure. Referring to step 2036, when the-predetermined time period has elapsed, the process 2000 proceeds to step 2038. At step 2038, the second pump 1726 is again utilized to evacuate the area under the wound dressing 1706 to the high-negative-pressure state. At step 2040, it is determined if the treatment is completed. Responsive to a determination the treatment is not completed, the process 2000 repeats to step 2032. Responsive to a determination that the treatment is completed, the process 2000 ends at step 2022.

The previous Detailed Description is of embodiment(s) of the disclosure. The scope of the disclosure should not necessarily be limited by this Description. The scope of the disclosure is instead defined by the following claims and the equivalents thereof.

What is claimed is:

1. A wound-care system comprising:
   a first pump fluidly coupled to an oxygen source;
   an oxygen concentrator fluidly coupled to the first pump;
   a humidification system fluidly coupled to the oxygen concentrator;
   a wound dressing fluidly coupled to the humidification system and to an exudate chamber;
   a negative-pressure tube fluidly coupled to the exudate chamber;
   a first pressure sensor exposed to pressure in the negative-pressure tube;
   a second pressure sensor exposed to pressure between the oxygen concentrator and the wound dressing;
   a first valve disposed between the first pump and the oxygen concentrator, the first valve being operable to selectively direct flow of fluid from the first pump to at least one of the oxygen concentrator and the humidification system;
   a second valve disposed between the oxygen concentrator and the wound dressing, the second valve being operable to selectively vent the wound dressing to an exterior environment;
   a third valve disposed in the negative-pressure tube, the third valve being operable to selectively vent the wound dressing to the exterior environment; and
   wherein selective activation of the first pump, the first valve, the second valve, and the third valve facilitates delivery of at least one of individual, sequential, or simultaneous negative-pressure treatment and oxygen-rich fluid treatment to the wound via the wound dressing.

2. The wound-care system of claim 1, wherein:
   the negative-pressure tube is fluidly coupled to an inlet of the first pump; and
   a fourth valve is disposed in the negative-pressure tube.

3. The wound-care system of claim 1, comprising:
   a second pump fluidly coupled to the negative-pressure tube; and
   wherein selective activation of the first pump and the second pump facilitates delivery of at least one of individual, sequential, or simultaneous oxygen-rich fluid treatment and negative-pressure treatment.

4. The wound-care system of claim 3, wherein the second pump configured to apply negative pressure to a wound via the wound dressing.

5. The wound-care system of claim 3, wherein the first pump and the second pump are operated independently of each other.

6. The wound-care system of claim 1, wherein:
   the humidification system comprises a proton-exchange tube;
   oxygen-rich fluid is circulated through the proton-exchange tube; and
   an exterior of the proton-exchange tube is exposed to ambient fluid.

7. The wound-care system of claim 1, wherein the humidification system comprises a channel disposed in a disposable container, the channel containing sterile water through which oxygen-rich fluid discharged from the oxygen concentrator.

8. The wound-care system of claim 1, wherein the oxygen concentrator is a pressure-swing adsorption device.

9. The wound-care system of claim 1, further comprising a disposable canister arranged upstream of the wound dressing.

10. A wound-care system comprising:
    a first pump fluidly coupled to an oxygen source;
    a humidification system fluidly coupled to the first pump; and
    a wound dressing fluidly coupled to the humidification system and to an exudate chamber;
    a negative-pressure tube fluidly coupled to the exudate chamber;

a first pressure sensor exposed to pressure in the negative-pressure tube;

a second pressure sensor exposed to pressure between the first pump and the wound dressing;

a first valve disposed between the first pump and the humidification system, the first valve being operable to selectively direct flow of fluid from the first pump to the humidification system; a second valve disposed between the first pump and the wound dressing, the second valve being operable to selectively vent the wound dressing to an exterior environment; a third valve disposed in the negative-pressure tube, the third valve being operable to selectively vent the wound dressing to the exterior environment; and wherein selective activation of the first pump, the first valve, and the second valve, facilitates delivery of at least one of individual, sequential, or simultaneous negative-pressure treatment and oxygen-rich fluid treatment to the wound via the wound dressing.

11. The wound-care system of claim 10, wherein:

the negative-pressure tube is fluidly coupled to an inlet of the first pump; and a fourth valve is disposed in the negative-pressure tube.

12. The wound-care system of claim 10, comprising:

a second pump fluidly coupled to the negative-pressure tube; and wherein selective activation of the first pump and the second pump facilitates delivery of at least one of individual, sequential, or simultaneous oxygen-rich fluid treatment and negative-pressure treatment to the wound via the wound dressing.

13. The wound-care system of claim 10, wherein the oxygen source is an oxygen concentrator.

* * * * *